(12) United States Patent
Lizardi et al.

(10) Patent No.: US 9,724,171 B2
(45) Date of Patent: Aug. 8, 2017

(54) METHODS, SYSTEMS, AND DEVICES FOR GAUGING A BONE TUNNEL

(71) Applicant: Medos International Sarl, Le Locle (CH)

(72) Inventors: Jose E. Lizardi, Walpole, MA (US); David B. Spenciner, North Attleboro, MA (US); Jonathan Correia, Boston, MA (US); Karthik Lavakumar, Framingham, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 26 days.

(21) Appl. No.: 14/996,737

(22) Filed: Jan. 15, 2016

(65) Prior Publication Data

US 2016/0193007 A1    Jul. 7, 2016

Related U.S. Application Data

(62) Division of application No. 13/799,303, filed on Mar. 13, 2013, now Pat. No. 9,271,801.

(51) Int. Cl.
*A61B 17/17* (2006.01)
*A61B 90/00* (2016.01)
*A61F 2/08* (2006.01)

(52) U.S. Cl.
CPC .............. *A61B 90/06* (2016.02); *A61B 90/00* (2016.02); *A61F 2/0805* (2013.01); *A61B 17/1714* (2013.01); *A61B 17/1764* (2013.01); *A61B 2090/061* (2016.02); *A61B 2090/062* (2016.02); *A61F 2002/0852* (2013.01); *A61F 2002/0882* (2013.01); *A61F 2250/0097* (2013.01)

(58) Field of Classification Search
CPC .................... A61B 2090/061; A61B 2090/062
See application file for complete search history.

(56) References Cited

U.S. PATENT DOCUMENTS

| | | |
|---|---|---|
| 5,139,520 A | 8/1992 | Rosenberg |
| 5,306,301 A | 4/1994 | Graf et al. |
| 5,374,269 A | 12/1994 | Rosenberg |
| 5,409,493 A | 4/1995 | Greenberg |
| 5,423,823 A | 6/1995 | Schmieding |
| 5,800,440 A | 9/1998 | Stead |
| 5,895,389 A | 4/1999 | Schenk et al. |
| 7,160,305 B2 | 1/2007 | Schmieding |
| 7,165,336 B2 | 1/2007 | Kim |
| 7,175,632 B2 | 2/2007 | Singhatat et al. |

(Continued)

*Primary Examiner* — David Bates

(57) ABSTRACT

Devices, systems, and methods are provided for gauging a bone tunnel. In one exemplary embodiment, a graft repair system can include an elongate pin, an elongate pusher shaft configured to be positioned over one opposed end of the pin when the pin is positioned within a bone tunnel, and a gauge member configured to be positioned over another opposed end of the pin when the pin is positioned within the bone tunnel. When the pusher shaft abuts the bone adjacent one of the open ends of the bone tunnel and the gauge member abuts the bone adjacent the other open end of the bone tunnel, an indicator mark on the pin can be visible through one or more windows formed in the gauge member. The indicator mark's position relative to each of the one or more windows can indicate one or more characteristics related to the bone tunnel.

6 Claims, 15 Drawing Sheets

(56) References Cited

U.S. PATENT DOCUMENTS

| | | |
|---|---|---|
| 7,444,756 B2 | 11/2008 | Kim |
| 7,607,238 B2 | 10/2009 | Kim et al. |
| 7,730,629 B2 | 6/2010 | Kim |
| 7,895,762 B2 | 3/2011 | Kim et al. |
| 7,988,697 B2 | 8/2011 | Miller et al. |
| 9,314,332 B2 * | 4/2016 | Mckernan ............ A61F 2/0811 |
| 2004/0092936 A1 * | 5/2004 | Miller ................ A61B 17/1714 |
| | | 606/916 |
| 2006/0264947 A1 | 11/2006 | Orbay et al. |
| 2006/0264956 A1 * | 11/2006 | Orbay ................ A61B 17/1615 |
| | | 606/80 |
| 2007/0250067 A1 * | 10/2007 | Schmieding ....... A61B 17/0401 |
| | | 606/96 |
| 2008/0188935 A1 * | 8/2008 | Saylor ................ A61B 17/0401 |
| | | 623/13.14 |
| 2008/0306408 A1 * | 12/2008 | Lo ........................ A61B 5/1076 |
| | | 600/587 |
| 2009/0005786 A1 * | 1/2009 | Prien ................... A61B 5/1076 |
| | | 606/102 |
| 2009/0228015 A1 * | 9/2009 | Ellis .................. A61B 17/8897 |
| | | 606/87 |
| 2010/0145340 A1 | 6/2010 | Phan et al. |
| 2012/0109132 A1 | 5/2012 | Ellis et al. |
| 2012/0330323 A1 | 12/2012 | Lizardi et al. |
| 2014/0276884 A1 | 9/2014 | Lizardi et al. |

\* cited by examiner

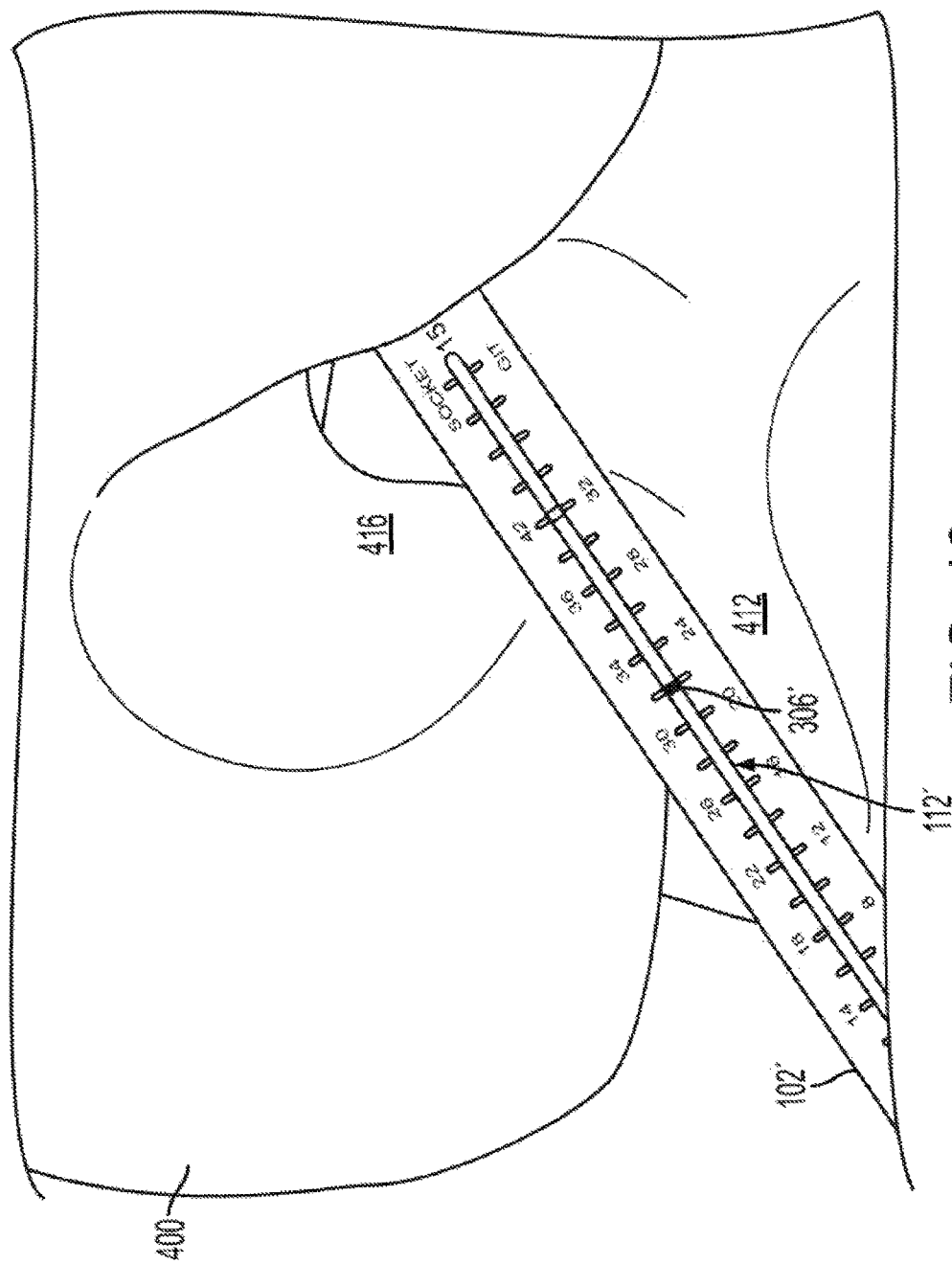

METHODS, SYSTEMS, AND DEVICES FOR GAUGING A BONE TUNNEL

The present application is a divisional of U.S. patent application Ser. No. 13/799,303, filed on Mar. 13, 2013, and entitled "METHODS, SYSTEMS, AND DEVICES FOR GAUGING A BONE TUNNEL," which is hereby incorporated by reference in its entirety.

CROSS REFERENCE TO RELATED APPLICATION

Field

The present disclosure relates generally to methods, systems, and devices for gauging a bone tunnel.

BACKGROUND

Injuries to ligaments are commonly treated using surgical procedures that involve forming a bone tunnel and placing a replacement graft in the tunnel. For example, treatment of a damaged anterior cruciate ligament (ACL) in a knee can include placing a replacement graft through a tunnel prepared in a femur. The tunnel is typically prepared in the femur from a position at or near the trochlear notch up through a portion of the femur and exiting through a side of the femur at a superior location. A graft is typically looped over a loop attached to a button. The button is able to pass in one direction up through the tunnel and then out adjacent a superior end of the tunnel. The button is typically reoriented such that it will not pass back through the tunnel and is typically positioned against the femur with the loop and graft hanging down into the tunnel therefrom. The tunnel has sufficient diameter at its inferior portion to accommodate the graft. The tunnel is typically made narrower at the superior portion, which carries only the loop and not the graft, to minimize bone removal.

Determining a proper depth of the inferior portion of the tunnel, and consequently also determining a proper size of the graft to position therein, quickly, accurately, and easily can be difficult because the inferior portion of the tunnel is "hidden" within the femur. Typically, a surgeon must use a total length of bone stock and preferred length of graft in tunnel to arrive at which loop length button to pick and at least how far to drill the femoral socket. However, these rely on estimations, and these determinations take time during the surgical procedure. The surgical procedure thus stalls until the correct calculations and determinations are made. Additionally, inadvertent mathematical errors can occur in calculating a minimum depth of the femoral socket and/or determining the loop size, which can further prolong the length of the surgical procedure.

Accordingly, there remains a need for improved methods, systems, and devices for gauging a bone tunnel.

SUMMARY

In one embodiment, a surgical system is provided that includes an elongate pin having an indicator mark thereon at a predetermined location, an elongate pusher shaft having a bore formed therein, and an elongate gauge member having a passageway formed therein, having a window formed therein that exposes at least a portion of the passageway, and having indicia formed thereon. When the pin is positioned through a bone tunnel formed in a bone with a first portion of the pin extending out from a first end of the bone tunnel and a second portion of the pin extending out from a second end of the bone tunnel, when the pusher shaft is disposed over the first portion of the pin and abuts a surface of the bone adjacent the first end of the bone tunnel, and when the gauge member is disposed over the second portion of the pin and abuts a surface of the bone adjacent the second end of the bone tunnel, a position of the indicator mark within the window relative to the indicia indicates a characteristic of the bone tunnel.

The characteristic can be at least one of a total depth of the bone tunnel, a depth of a portion of the bone tunnel (e.g., a portion of the bone tunnel adjacent the second end of the bone tunnel) having a larger diameter than another portion of the bone tunnel (e.g., a portion of the bone tunnel adjacent the first end of the bone tunnel), and an amount of interface between a graft and the bone tunnel.

The pin can vary in any number of ways. For example, the second portion of the pin can be configured to be seated within the passageway in a clearance fit.

The gauge member can also vary in any number of ways. For example, the window can include a slot extending longitudinally along the gauge member. For another example, the window can include a first window, the indicia can include first indicia that is associated with the first window and that indicates a property of an implant having a first size, the gauge member can include a second window formed therein that exposes at least a portion of the passageway, and the gauge member can include second indicia that is associated with the second window and that indicates a property of an implant having a second size that is different than the first size. For another example, the characteristic can include one of a total depth of the bone tunnel, an amount of interface between a graft and the bone tunnel, and a depth of a portion of the bone tunnel adjacent the second end of the bone tunnel having a diameter greater than a diameter of another portion of the bone tunnel adjacent the first end of the bone tunnel. The gauge member can have second indicia formed thereon, and a position of the indicator mark within the window relative to the second indicia can indicate another one of the total depth of the bone tunnel, the amount of interface between the graft and the bone tunnel, and the depth of the portion of the bone tunnel. For yet another example, the gauge member can have a second window formed therein, can have third indicia formed thereon, and can have fourth indicia formed thereon. A position of the indicator mark within the second window relative to the third indicia can indicate one of the total depth of the bone tunnel, the amount of interface between the graft and the bone tunnel, and the depth of the portion of the bone tunnel. A position of the indicator mark within the second window relative to the fourth indicia can indicate another one of the total depth of the bone tunnel, the amount of interface between the graft and the bone tunnel, and the depth of the portion of the bone tunnel. For another example, the indicia and the second indicia can be calibrated to a size of a first implant configured to abut the surface of the bone adjacent the first end of the bone tunnel when the graft is positioned within the bone tunnel, and the third and fourth indicia can be calibrated to a size of a second implant configured to abut the surface of the bone adjacent the first end of the bone tunnel when the graft is positioned within the bone tunnel.

In another aspect, a surgical device is provided that in one embodiment includes an elongate gauge member having a passageway extending therethrough, having a window formed therein that exposes at least a portion of the passageway, and having indicia formed thereon adjacent the window. The gauge member is configured to be inserted into a body such that at least a portion of the window is disposed within the body, and the gauge member is configured to abut a surface of a bone within the body. The indicia corresponds to at least one of an implant size or a graft size.

The device can vary in any number of ways. For example, the gauge member can have a second window formed therein that exposes at least a portion of the passageway, and can have second indicia formed thereon adjacent the second window. The second indicia can correspond to at least one of a second, different implant size or a second, different graft size.

In another aspect, a surgical method is provided that in one embodiment includes advancing a pin through a tunnel formed in a bone such that a first portion of the pin extends outwardly from a first end of the tunnel, and a second portion of the pin extends outwardly from a second end of the tunnel. The method also includes positioning an elongate pusher shaft over the first portion of the pin and in abutment with a surface of the bone adjacent the first end of the tunnel, and advancing an elongate gauge member over the second portion of the pin and in abutment with a surface of the bone, and positioning an indicator mark formed on the pin within a window formed in the gauge member. A position of the indictor mark relative to the window indicates a characteristic related to the tunnel when the pusher shaft abuts the surface of the bone adjacent the first end of the tunnel and the gauge member abuts the surface of the bone adjacent the second end of the tunnel. The characteristic can be at least one of a total depth of the tunnel, a depth of a portion of the tunnel having a larger diameter than another portion of the tunnel, and an amount of interface between a graft and the tunnel.

The method can have any number of variations. For example, the method can include selecting a size of a graft to position within the tunnel based on the position of the indictor mark relative to the window, and advancing the graft having the selected size into the tunnel. For another example, the method can include adjusting the gauge member relative to the pin. A position of the indictor mark relative to a second window formed in the gauge member can indicate another characteristic related to the tunnel when the pusher shaft abuts the surface of the bone adjacent the first end of the tunnel and the gauge member abuts the surface of the bone adjacent the second end of the tunnel. For another example, positioning the pusher shaft can include pushing the pin and the pusher shaft toward the second end of the tunnel. For yet another example, advancing the gauge member can include passing the pin through a cannulated interior of the gauge member.

BRIEF DESCRIPTION OF DRAWINGS

This invention will be more fully understood from the following detailed description taken in conjunction with the accompanying drawings, in which:

FIG. 19 is another perspective view of the gauge member of FIG. 17 with the gauge member abutting the femur.

DETAILED DESCRIPTION

Figure 1:
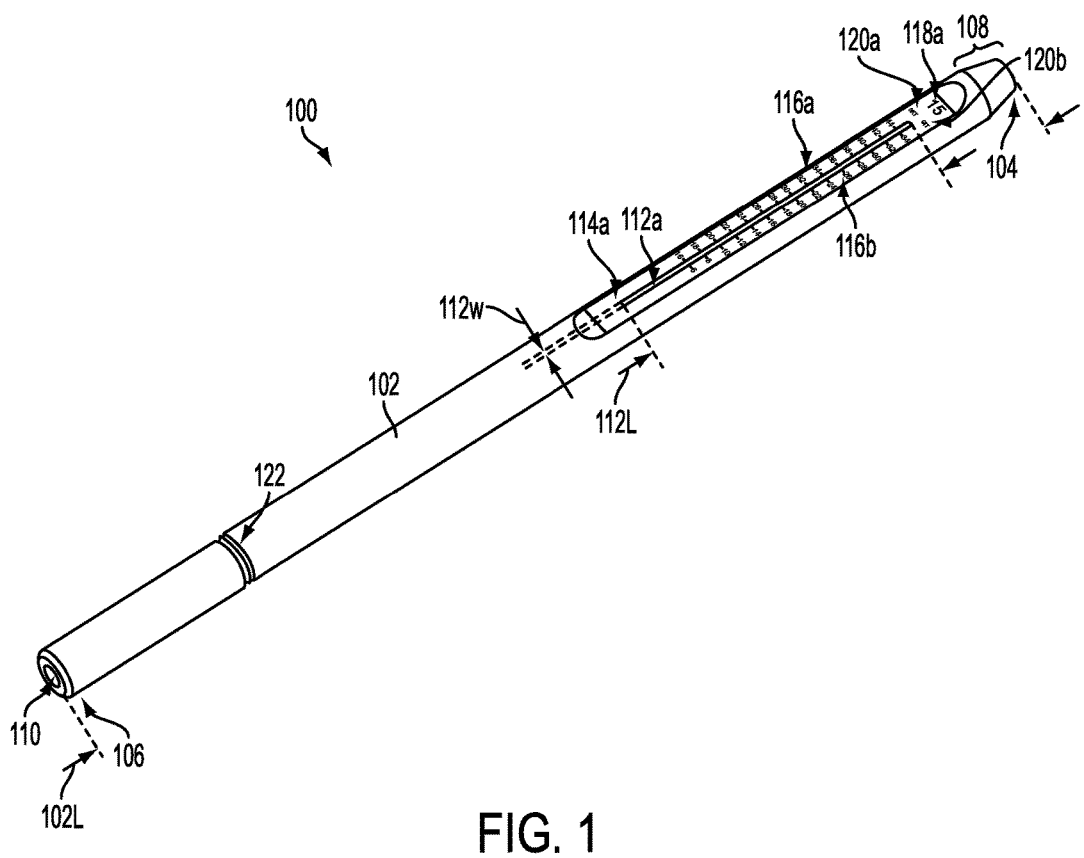
FIG. 1 is a perspective view of one embodiment of a gauge member.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary devices, systems, and methods are provided for gauging a bone tunnel. In general, the devices, systems, and methods can allow one or more characteristics of a bone tunnel and/or a size of a graft to be positioned within the bone tunnel to be determined without any guesswork or mathematical calculations. In one exemplary embodiment, a system can include a pin, a pusher shaft, and a gauge member. The pin can be configured to be positioned within a bone tunnel with opposed ends thereof extending out opposed open ends of the bone tunnel, the pusher shaft can be configured to be positioned over one of the opposed ends of the pin when the pin is positioned within the bone tunnel, and the gauge member can be configured to be positioned over the other opposed end of the pin when the pin is positioned within the bone tunnel. When the pusher shaft abuts the bone adjacent one of the open ends of the bone tunnel and the gauge member abuts the bone adjacent the other open end of the bone tunnel, an indicator mark on the pin can be visible through one or more windows formed in the gauge member. The indicator mark's position relative to the window(s), e.g., to one or more scales on the gauge member adjacent the window(s), can indicate one or more characteristics related to the bone tunnel, such as a total depth of the bone tunnel, a depth of a socket portion to be formed in the bone tunnel, and/or a size of a graft to be positioned within the socket portion of the bone tunnel. Thus, any one or more of a total depth of the bone tunnel, a partial depth of the bone tunnel, and a size of a graft to be positioned within the bone tunnel can be determined without any guesswork or mathematical calculations. Each of the one or more windows can correspond to a differently sized implant configured to be implanted within a patient's body, such as elongate bar coupled to a loop having a graft looped thereover. The indicator mark's position relative to each of the one or more windows can indicate one or more characteristics related to the bone tunnel that are specific to the implant corresponding to the window. Different implants can therefore be easily and quickly compared during performance of a surgical procedure, which can help save time and/or help optimize selection of appropriately sized elements, e.g., differently sized grafts, differently sized socket-forming bone drills, and differently sized implants, to be implanted within a patient. The one or more windows can thus allow the system to be used with a variety of patients each having different anatomies for which differently sized implants and/or differently sized grafts would be appropriate.

As indicated above, a bone tunnel can be configured to receive a graft therein. Various grafts can be used based on any one or more of a patient, a size and shape of a bone tunnel, a size and shape of damaged tissue, and/or other factors. By way of example, a graft can include a tendon graft or ligament graft formed from autologous tissue harvested from elsewhere in a patient's body, an allograft, an artificial graft, or a tissue-engineered living replacement. Generally, a folded graft can range from 5 mm to 12 mm thick and from 80 mm to 200 mm long.

The pins, pusher shafts, and gauge members discussed herein can be used in a variety of surgical procedures in which a graft is secured within a tunnel formed in a bone, such as a procedure for attaching tissue to bone, e.g., ACL repair, rotator cuff repair, etc. In an exemplary embodiment, a procedure including use of a pin, a pusher shaft, and a gauge member can be a minimally invasive procedure, but as will be appreciated by a person skilled in the art, the pins, pusher shafts, and gauge members discussed herein also have application in open surgical instrumentation as well as application in robotic-assisted surgery.

In an exemplary embodiment, a pin, a pusher shaft, and a gauge member can be configured to be used in a surgical procedure that includes implanting an implant within a patient to facilitate attachment of tissue to bone. The implant can have a variety of sizes, shapes, and configurations. In an exemplary embodiment, the implant can include an elongated body configured to have graft attached thereto and to be passed through a bone tunnel in a first position relative to the bone tunnel. Then, with the graft positioned in the bone tunnel and the implant located outside of the bone tunnel, the implant can be rotated relative to the bone tunnel so as to secure the graft within the bone tunnel with the implant abutting the bone outside the bone tunnel. Examples of the implant as an elongated body include graft attachment devices such as the Endobutton CL fixation device (available from Smith & Nephew, Inc. of London, UK) and the graft attachment devices described in U.S. Pat. No. 5,306,301 entitled "Graft Attachment Device And Method Of Using Same" issued Apr. 26, 1994.

Figure 2:
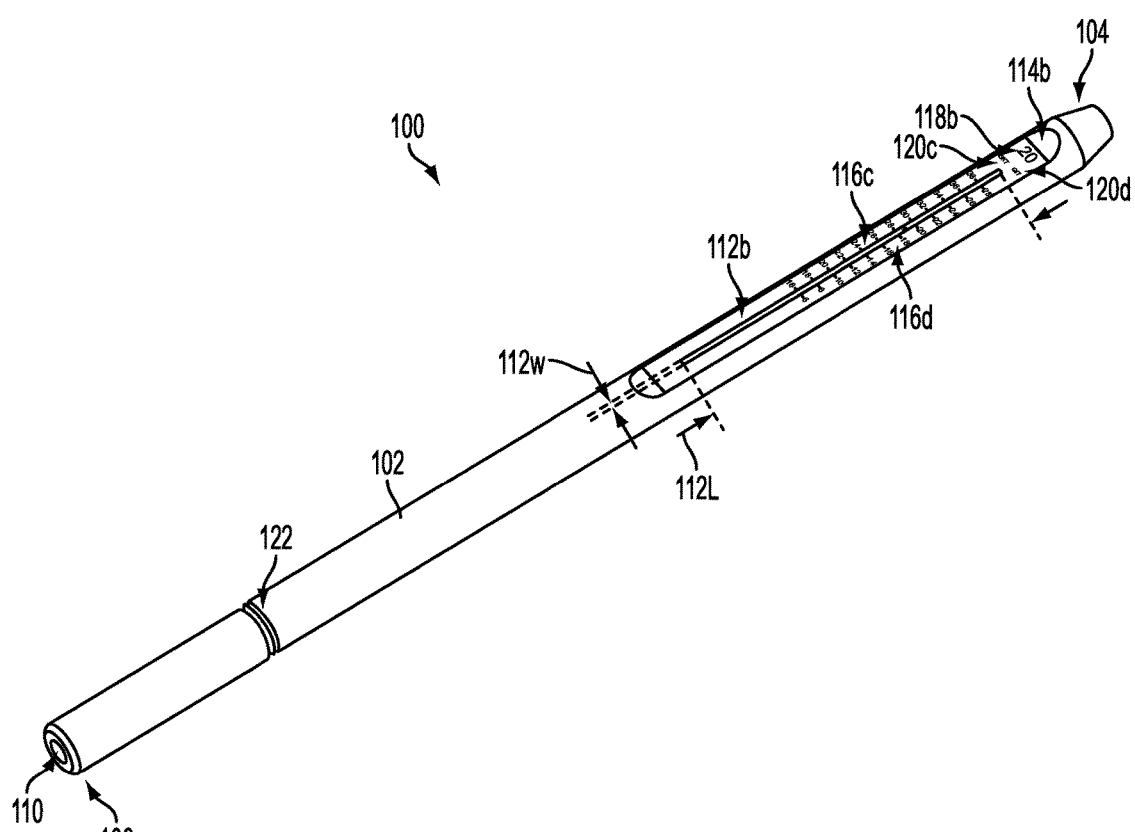
FIG. 2 is another perspective view of the gauge member of FIG. 1.

A gauge member can have a variety of sizes, shapes, and configurations. FIGS. 1 and 2 illustrates one exemplary embodiment of a gauge member 100. The gauge member 100 can be elongate and can include a shaft 102 having a first end 104 and a second end 106. The shaft 102 has a circular cross-sectional shape in the illustrated embodiment, which can facilitate smooth advancement of at least a portion of the shaft 102 through tissue, e.g., through tissue adjacent a bone having a bone tunnel formed therein. However, the shaft 102 can have other cross-sectional shapes, e.g., ovular, octagonal, etc. The shaft 102 can have a constant diameter along a longitudinal length 102L thereof, or, as in the illustrated embodiment, the shaft 102 can have different diameters at various portions along its longitudinal length 102L. An end portion 108 of the shaft 102 adjacent the first end 104 can be tapered down in a direction away from the second end 106 such that the shaft's end portion 108 can have a variable diameter. The tapered end portion 108 can facilitate smooth advancement of the end portion 108, and a trailing portion of the shaft 102, through tissue.

The gauge member 100 can have an inner lumen or passageway 110 extending therethrough between the first and second ends 104, 106 of the shaft 102. The gauge member 100 can thus be cannulated. Being cannulated can allow a pin to extend through the gauge member 100, as discussed further below. The passageway 110 can have a cross-sectional shape that corresponds to a pin configured to be advanced therethrough. The passageway 110 has a circular cross-sectional shape in the illustrated embodiment, which can facilitate passage of a cylindrical pin therethrough. The passageway 110 can have other cross-sectional shapes, same or different from the cross-sectional shape of the shaft 102. In an exemplary embodiment, a diameter of the passageway 110 can be constant along a longitudinal length thereof, e.g., along the longitudinal length 102L of the shaft 102. The constant diameter of the passageway 110 can facilitate clearance fit seating of a pin therein, as discussed further below. Also, the diameter of the passageway 110, and hence the diameter of the shaft 102 through which the passageway 110 extends, having a larger diameter than the pin can allow the pin to pass through a bone tunnel while preventing the gauge member 100 from passing through the bone tunnel. In other words, the bone tunnel can have a diameter greater than the diameter of the pin and less than the diameter of the gauge member 100, at least at an end of the end portion 108, such that the pin can enter the bone tunnel and the gauge member 100 cannot enter the bone tunnel.

The gauge member 100 can have one or more windows 112a, 112b formed therein that each expose at least a portion of the passageway 110. Each of the one or more windows 112a, 112b can have a variety of sizes, shapes, and configurations. The gauge member 100 in the illustrated embodiment includes two window 112a, 112b, but the gauge member 100 can include a plurality of windows formed therein, e.g., two, three, four, five, etc. In an exemplary embodiment, a gauge member can include two windows formed therein. If a gauge member includes a plurality of windows formed therein, the windows can be arranged radially around a circumference or perimeter of the gauge member's shaft. The windows can be equidistantly spaced apart from one another around the circumference or perimeter of the shaft, as in the illustrated embodiment of FIGS. 1 and 2. Providing equidistantly spaced windows can help maintain structural stability of the shaft by not having any two or more windows spaced close enough to one another such that a portion of the shaft therebetween becomes weak, fractures, and/or breaks, and/or can help reduce confusion as to which window is being viewed through to visualize the passageway 110 and/or a tool received therein. As discussed further below, if a gauge member includes a plurality of windows formed therein, each of the windows can correspond to a differently sized implant. In this way, a single gauge member can facilitate comparison of differently sized implants, which can facilitate quick decision-making during performance of a surgical procedure. As also discussed further below, each of a gauge member's plurality of windows can include one or more scales each associated with the same characteristic(s). The differently sized implants associated with each of the windows can thus be easily compared against one another with respect to the same characteristic(s).

Figure 1A:
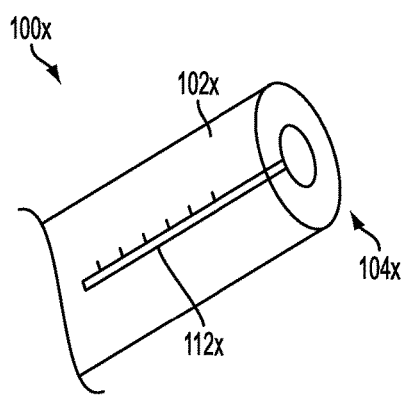
FIG. 1A is a perspective, partial view of another embodiment of a gauge member.

As in the illustrated embodiment, the one or more windows 112a, 112b can each be in the form of a cut-out formed through a sidewall of the shaft 102 and exposing the passageway 110. The cut-out can be formed through a sidewall of the shaft 102. The cut-out can have a variety of sizes, shapes, and configurations. In an exemplary embodiment, the cut-out can extend longitudinally along a partial longitudinal length 112L of the shaft's longitudinal length 102L. The partial longitudinal length 112L can extend along any partial portion of the shaft's longitudinal length 102L. In the illustrated embodiment, each of the windows 112a, 112b has a same longitudinal length 112L. However, if a gauge member includes a plurality of windows, each of the windows can extend along a different longitudinal length therealong. The cut-out can have an enclosed perimeter defined by the shaft 102, e.g., the cut-out can have an enclosed shape. In the illustrated embodiment, each of the one or more windows 112a, 112b includes a cut-out having an enclosed shape positioned in an intermediate portion of the shaft 102 between the first and second ends 104, 106, and are each in the form of a longitudinal slot extending along the partial longitudinal length 112L of the shaft's longitudinal length 102L. In another embodiment, a gauge member's cut-out can extend through one or both ends of the gauge member's shaft such that the cut-out does not have an enclosed shape. FIG. 1A illustrates an embodiment of a gauge member 100x that includes a window 112x in the form of a cut-out that extends through an end 104x of the gauge member's shaft 102x.

In another embodiment, a gauge member can include one or more windows each in the form of a transparent or semi-transparent portion of a shaft of the gauge member. In other words, at least a portion of the shaft can be formed from one or more transparent or semi-transparent materials. The transparent or semi-transparent portion of the shaft can allow visualization through the shaft's sidewall of a passageway extending through the shaft. In this way, a pin received in the passageway can be visualized through one or more windows, e.g., through the transparent or semi-transparent portion(s) of the shaft. If a gauge member includes a plurality of windows, each of a gauge member's windows can be a cut-out or each can be a transparent or semi-transparent portion of the gauge member's shaft, which can facilitate manufacture of the gauge member. However, if a gauge member includes a plurality of windows, at least one of the windows can be a cut-out while at least one other of the windows can be a transparent or semi-transparent portion of the gauge member's shaft.

Referring again to FIG. 1, the one or more windows 112a, 112b can each be formed in one or more recessed portions 114a, 114b of the sidewall of the shaft 102. If the gauge member 100 includes a plurality of windows 112a, 112b, the shaft 102 can have one recessed portion in which all of the plurality of windows 112a, 112b are located. Alternatively, as in the illustrated embodiment, each of the plurality of windows 112a, 112b can have its own recessed portion 114a, 114b. The one or more recessed portions 114a, 114b can facilitate visualization of the one or more windows 112a, 112b and indicia adjacent thereto, discussed further below, when the gauge member 100 is positioned within a patient's body by helping to provide clearance space between adjacent tissue and the one or more windows 112a, 112b and the indicia.

The one or more windows 112a, 112b can be open, as in the illustrated embodiment, such that the one or more windows 112a, 112b can be in communication with the passageway 110. Having an open window can facilitate manufacture of the gauge member 110, e.g., by casting or molding a metal. The one or more windows 112a, 112b can optionally include a transparent or semi-transparent cover (not shown) seated therein, similar to glass in a window pane. The cover can be configured to help keep the passageway 110 clear by preventing fluid and other matter from unintentionally entering or exiting the passageway 110 through the one or more windows 112a, 112b. The pin, another surgical tool, and/or other matter inserted into the passageway 110 can thus be less likely to encounter an obstruction preventing passage therethrough and/or can be less likely to unintentionally exit the passageway 110 through the one or more windows 112a, 112b. If a gauge member includes a plurality of windows, any one or more of the windows can include a cover.

The one or more windows 112a, 112b can have a maximum width 112w less than or equal to the diameter of the passageway 110 and less than a minimum diameter of a surgical tool, e.g., a pin, configured to be passed through the passageway 110. In this way, the one or more windows 112a, 112b can be configured to help prevent the surgical tool positioned within the passageway 110 from passing through the any of the one or more windows 112a, 112b. The surgical tool can thus be less likely to poke through any of the one or more windows 112a, 112b and damage tissue and/or other material near the gauge member 100, and/or can be more likely to be predictably positioned within the passageway 110, which can facilitate comparison of the tool and the indicia, as discussed further below.

The one or more windows 112a, 112b can be positioned near the first end 104 of the shaft 102, as shown in the illustrated embodiment. Being positioned near the shaft's first end 104 can facilitate visualization of a pin through the one or more windows 112a, 112b and/or can help ensure that the one or more windows 112a, 112b are at least partially disposed within a patient's body when the first end 104 of the shaft 102 abuts a bone, as discussed further below.

The one or more windows 112a, 112b can each be associated with a specific size of an implant configured to be implanted within a patient's body to facilitate attachment of tissue to bone, such as elongate bar coupled to a loop, e.g., a suture, having a graft looped thereover. If the gauge member includes a plurality of windows, in an exemplary embodiment, each of the windows can be associated with a different implant size. The gauge member 100 can include one or more size indicators 118a, 118b that indicate the specific size of the implant associated with the one or more windows 112a, 112b. In an exemplary embodiment, the one or more windows 112a, 112b can be associated with an implant having a size in a range of 10 to 60 mm, e.g., 15 mm, 20 mm, etc. The one or more size indicators 118a, 118b in the illustrated embodiment include a number on the shaft 102 adjacent their respective ones of the windows 112a, 112b. The number can reflect the implant's specific loop size, which in the illustrated embodiment is "15" (for a 15 mm size loop) for the first scale 112a and is "20" (for a 20 mm size loop) for the second scale 112b. The one or more size indicators 118a, 118b can have other forms, such as a word, alphanumeric text, a product identification code, a color coded symbol, etc., that specifically identifies a size of an implant's loop and/or a specific type of implant. The one or more size indicators 118a, 118b are positioned above their associated windows 112a, 112b in the illustrated embodiment, but any one or more of the one or more size indicators 118a, 118b can be located elsewhere, e.g., below its associated window 112a, 112b, to a side of its associated window 112a, 112b, etc.

By being associated with a specific size of an implant, the one or more windows 112a, 112b can facilitate identification of one or more characteristics relevant to use of an implant having that specific size in a surgical procedure. The indicia adjacent the one or more windows 112a, 112b can facilitate identification of the one or more characteristics. The gauge member's indicia can have a variety of configurations.

In an exemplary embodiment, the indicia can include one or more scales on the shaft 102 adjacent the one or more windows 112a, 112b. The gauge member 100 in the illustrated embodiment includes a first scale 116a and a second scale 116b associated with the first window 112a, and a third scale 116c and a fourth scale 116d associated with the second window 112b. However, a window can have any number of scales associated therewith. In an exemplary embodiment, a window has one or two scales associated therewith. Each of the one or more scales 116a, 116b, 116c, 116d associated with the one or more windows 112a, 112b can extend longitudinally along the shaft's longitudinal length 102L adjacent its associated window 112a, 112b. The one or more scales 116a, 116b, 116c, 116d associated with the one or more windows 112a, 112b can each be calibrated for the specific implant size associated with the one or more windows 112a, 112b, e.g., the implant size indicated by the one or more size indicators 118a, 118b. In an exemplary embodiment, each of the one or more scales 116a, 116b, 116c, 116d can correspond to one characteristic associated with the size of the implant indicated by the one or more size indicators 118a, 118b. The characteristic can facilitate selection of one or more elements, e.g., a graft, an implant, a drill size, etc., to be used with a particular patient during performance of a surgical procedure on the patient. Examples of characteristics include a depth of a socket of a bone tunnel (e.g., a depth of an enlarged diameter portion of a bone tunnel), a total bone tunnel depth, a graft in tunnel (GIT) or graft/tunnel (GT) interface depth, etc.

In the illustrated embodiment, the first and third scales 116a, 116c each correspond to socket depth (shown in millimeters), and the second and fourth scales 116b, 116d each correspond to GT interface depth (shown in millimeters). The first scale 116a indicating socket depth for a 15 mm implant in the illustrated embodiment ranges from 16 to 44 mm in 2 mm increments. The second scale 116b indicating GT interface depth for a 15 mm implant in the illustrated embodiment ranges from 6 to 34 mm in 2 mm increments. The third scale 116c indicating socket depth for a 20 mm implant in the illustrated embodiment ranges from 16 to 38 mm in 2 mm increments. The fourth scale 116d indicating GT interface depth for a 20 mm implant in the illustrated embodiment ranges from 6 to 28 mm in 2 mm increments. In the illustrated embodiment, the socket depth and the GT interface depth are calibrated with a 10 mm difference therebetween. In other words, the first and third scales 116a, 116c indicating socket depth are 10 mm larger than their respective corresponding second and fourth scales 116b, 116d indicating GT interface depth. As discussed further below, this 10 mm difference can reflect that a graft does not fully occupy a socket and/or that an implant can be passed through a bone tunnel in a first position relative thereto and can require a clearance distance to be rotated outside the bone tunnel from the first position to a second, different position such that the implant can be positioned outside the bone tunnel and hold a graft within the bone tunnel. Although the illustrated embodiment has a 10 mm calibrated difference between the socket depth and the GT interface depth, the calibrated difference can be another distance, such as in a range of about 2 to 12 mm, e.g., 6 mm, 7 mm, 8.5 mm, 11 mm, etc.

The gauge member's indicia can include one or more scale identifiers. Each of the one or more scale identifiers can be associated with one of the gauge member's scales and can be configured to identify the characteristic indicated by its associated scale. The gauge member 100 in the illustrated embodiment includes a first scale identifier 120a associated with the first scale 116a, a second scale identifier 120b associated with the second scale 116b, a third scale identifier 120c associated with the third scale 116c, a fourth scale identifier 120d associated with the fourth scale 116d. The first and third scale identifiers 120a, 120c are "SKT" and the second and fourth scale identifiers 120b, 120d are "GIT" in the illustrated embodiment, but the scale identifiers can include other text, symbol, color, etc. The one or more scale identifiers 120a, 120b, 120c, 120d are positioned above each of their respective scales 116a, 116b, 116c, 116d in the illustrated embodiment, but the one or more scale identifiers 120a, 120b, 120c, 120d can be located elsewhere, e.g., below their respective scales 116a, 116b, 116c, 116d, to a side of their respective scales 116a, 116b, 116c, 116d, etc.

The one or more windows 112a, 112b in the illustrated embodiment are each associated with a single implant size, but a window can be associated with a plurality of implant sizes. For example, a window can be associated with two implant sizes and can have two scales adjacent thereto. Each of the scales can be associated with one of the implant sizes. In an exemplary embodiment, each of the scales can correspond to a same characteristic associated with its associated implant size, which can facilitate comparison of the different implant sizes against one another with respect to the same characteristic.

The gauge member 100 can include a depth indicator 122 formed on or formed in the shaft 102. The depth indicator 122 can be configured to be visualized when the gauge member 100 is disposed within a patient's body to facilitate determination of the gauge member's depth with the patient's body. In an exemplary embodiment, the depth indicator 122 becoming visible within a patient's body can indicate that a majority portion of the gauge member 100 is disposed within the patient's body and that, therefore, additional insertion of the gauge member 100 into the patient's body may not be advisable or possible. The depth indicator 122 can be located between the window 112 and the second end 106 of the shaft 102. The depth indicator 122 is in the form of a circumferential groove in the illustrated embodiment, but the depth indicator 122 can have other configurations, e.g., a dot, line, text, or other symbol or alphanumeric character(s) on the shaft 102.

Figure 3:
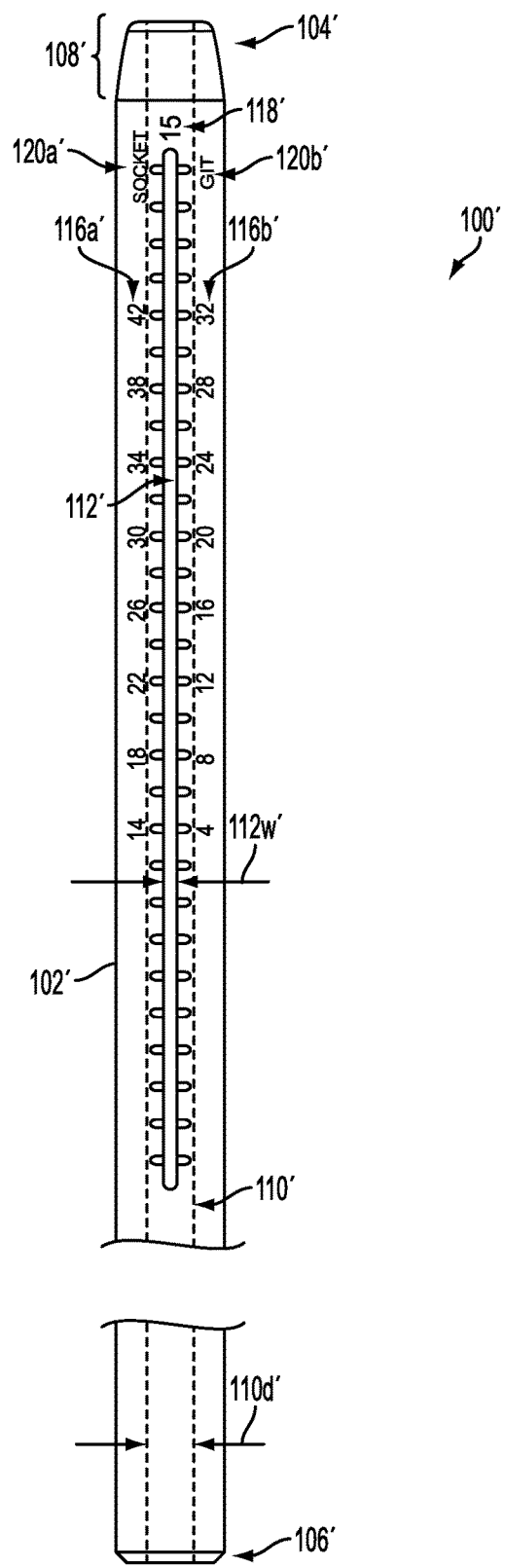
FIG. 3 is a side, partially transparent view of another embodiment of a gauge member.
Figure 4:
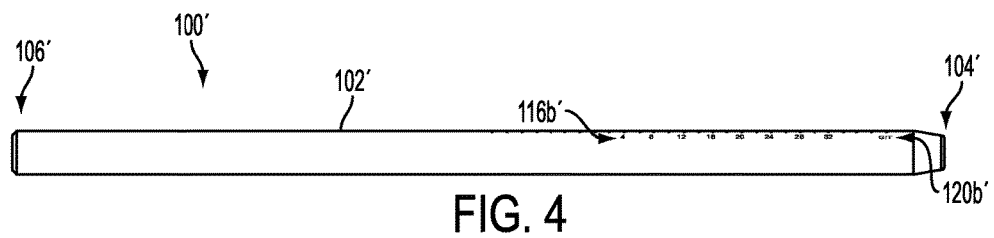
FIG. 4 is another side view of the gauge member of FIG. 3.

FIGS. 3 and 4 illustrate another exemplary embodiment of a gauge member 100'. The gauge member 100' can generally be configured and used similar to the gauge member 100 of FIGS. 1 and 2. In the illustrated embodiment, the gauge member 100' has an inner lumen or passageway 110' extending therethrough and includes a single window 112'. The window 112' has a maximum width 112w' less than a minimum diameter 110d' of the passageway 110'. The window 112' is in the form of a cut-out formed as a longitudinal slot in a sidewall of the gauge member's shaft 102'. The window 112' in this illustrated embodiment is not formed in a recessed portion of the shaft 102'. The window 112' corresponds to a 15 mm implant, as indicated by a size indictor 118', and has first and second scales 116a', 116b' associated therewith. The first scale 116a' indicates socket depth, as indicated by a first scale identifier 120a' ("SOCKET"), and ranges from 14 to 42 mm in 2 mm increments. The second scale 116b' indicating GIT, as indicated by a second scale identifier 120b ("GIT"), and ranges from 4 to 32 mm in 2 mm increments. The first and second scales 116a', 116b' are thus calibrated with a 10 mm difference.

Figure 5:
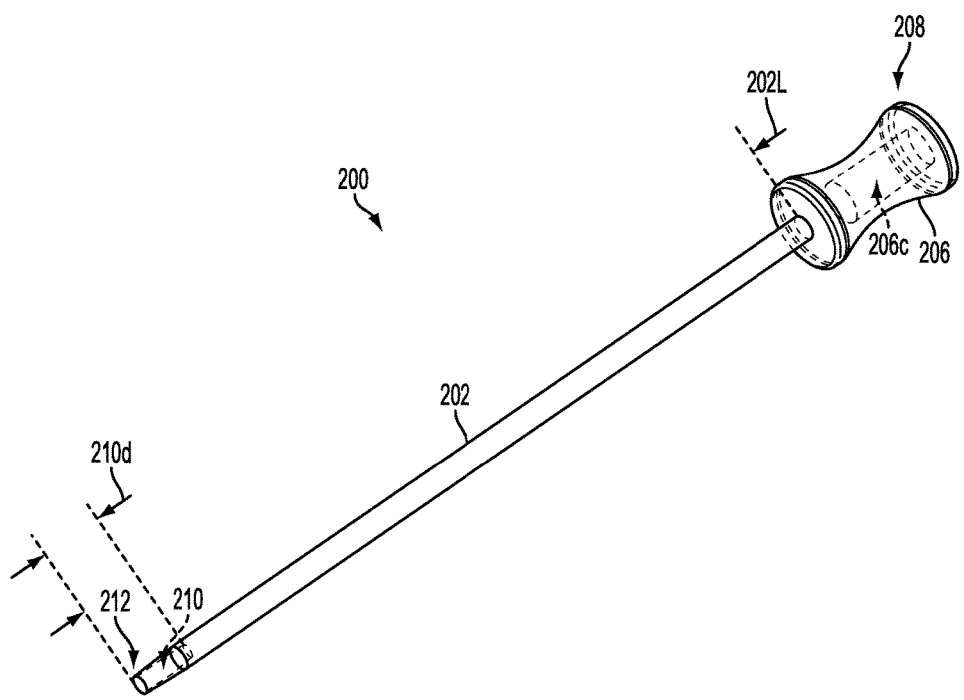
FIG. 5 is a perspective, partially transparent view of one embodiment of a pusher shaft.

A pusher shaft can have a variety of sizes, shapes, and configurations. FIG. 5 illustrates one exemplary embodiment of a pusher shaft 200. The pusher shaft 200 can be elongate and can include a handle 206 having a shaft 202 extending therefrom. The handle 206 can have a variety of sizes, shapes, and configurations. The handle 206 can be configured to be held by hand, thereby facilitating manipulation of the pusher shaft 200. In the illustrated embodiment, the handle 206 has a dumbbell shape and has a cavity 206c formed therein. However, the handle 206 can have a variety of other shapes and configurations, as will be appreciated by a person skilled in the art. In some embodiments, a pusher shaft need not include a handle, e.g., an end of the pusher shaft's shaft can be configured to be handled. The handle 206 can have a flat or planar end 208 such that the pusher shaft 200 can have a flat or planar end. The flat or planar end 208 can be configured to be pushed by hand and/or hit with a mallet, hammer, etc. to facilitate pushing of the pusher shaft 200 into and/or through tissue.

The cavity 206c can have a variety of sizes, shapes, and configurations. The cavity 206c has a cylindrical shape and circular cross-sectional shape in the illustrated embodiment, but the cavity 206c can have other shapes and cross-sectional shapes, e.g., cone-shaped, ovular cross-sectional shape, octagonal cross-sectional shape, etc. The cavity 206c can extend through the end 208 of the pusher shaft 200, e.g., through and end of the handle 206. The cavity 206c can be configured to receive a surgical tool (not shown) therein, such as a driver. In other words, the end of the pusher shaft 200 that has the cavity 206c formed therein can be configured to coupled to a surgical tool. The cavity 206c can be configured to allow the surgical tool to be removably and replaceably seated therein. The surgical tool, when seated within the cavity 206c, can facilitate pushing of the pusher shaft 200 into and/or through tissue.

The shaft 202 extending from the handle 206 can have a variety of sizes, shapes, and configurations. The shaft 202 has a circular cross-sectional shape in the illustrated embodiment, which can facilitate smooth advancement of at least a portion of the shaft 202 through tissue, e.g., through tissue adjacent a bone having a bone tunnel formed therein. However, the shaft 202 can have other cross-sectional shapes, e.g., ovular, octagonal, etc. The shaft 202 can have a constant diameter along a longitudinal length 202L thereof, or, as in the illustrated embodiment, the shaft 202 can have different diameters at various portions along its longitudinal length 202L. A tip portion 204 of the shaft 202 at an opposite end of the pusher shaft 200 from the handle 206 can be tapered in a direction away from the handle 206 such that the tip portion 204 can have a variable diameter. The tapered tip portion 204 being can facilitate smooth advancement of the tip portion 204, and a trailing portion of the shaft 202, through tissue.

The shaft 202 can include a bore 210 formed therein. The bore 210 can be formed at least partially within the tip portion 204 at an end 212 of the pusher shaft 200 opposite the flat or planar end 208, e.g., at an end opposite from the handle 206. In the illustrated embodiment, the bore 210 extends through an entirety of the tip portion 204 and into a portion of the shaft 202. The bore 210 can have a variety of sizes, shapes, and configurations. The bore 210 has a cylindrical shape and circular cross-sectional shape in the illustrated embodiment, but the bore 210 can have other shapes and cross-sectional shapes, e.g., cone-shaped, ovular cross-sectional shape, octagonal cross-sectional shape, etc. The bore 210 can extend through the end 212 of the pusher shaft 200. The bore 210 can be configured to receive a surgical tool (not shown) therein, such as a pin, as discussed further below. In other words, the end of the pusher shaft 200 that has the bore 210 formed therein can be configured to be coupled to a surgical tool. The bore 210 can be configured to allow the surgical tool to be removably and replaceably seated therein, and/or to allow the surgical tool to be seated therein without any mechanical connection element, e.g., complementary threads, an adhesive, a pushable button fit into a corresponding hole, etc., actively fixing or locking the pusher shaft 200 and the surgical tool together. Lacking such a mechanical connection element can allow the surgical tool to be quickly coupled to and quickly coupled from the pusher shaft 200, thereby saving time in a surgical procedure, and/or can allow the surgical tool to have a sharp end seatable within the bore 210 without damaging the pusher shaft 200. The pusher shaft 200 can be configured to couple to a surgical tool in other a variety of other ways, such as by being clamped thereto using one or more mechanical connection elements etc. at the pusher shaft's tip portion 204' etc. A pin seated within the bore 210, or otherwise coupled to the pusher shaft 200, can facilitate measurements using one or more scales on a gauge member, as discussed further below.

A depth 210d of the bore 210 can have a variety of values. In an exemplary embodiment, the depth 210d can be in range of about 5 to 10 mm, e.g., about 5 mm, about 10 mm, etc. The depth 210d can be relatively shallow such that a minimal amount of a pin is disposed within the bore 210 when the pin is fully seated within the bore 210. In this way, the pusher shaft 200 can be configured to engage a pin so as to be configured to push the pin, e.g., by pushing on the handle 206, while allowing almost an entirety of the pin to be outside of the pusher shaft 200. Thus, a longitudinal length of the pusher shaft 200 advanced into a patient's body can be minimized. The pin's shaft can have a smaller diameter than the pusher shaft 200, so the pin being disposed within the patient's body rather than the pusher shaft's shaft 202 can displace less tissue and/or be less likely to irritate or otherwise damage tissue. Also, the pusher shaft 200 having a larger diameter than the pin can allow the pin to pass through a bone tunnel while preventing the pusher shaft 200 from passing through the bone tunnel. In other words, the bone tunnel can have a diameter greater than the diameter of the pin and less than the diameter of the pusher shaft 200, at least at an end of the tip portion 204, such that the pin can enter the bone tunnel and the pusher shaft 200 cannot enter the bone tunnel.

Figure 6:
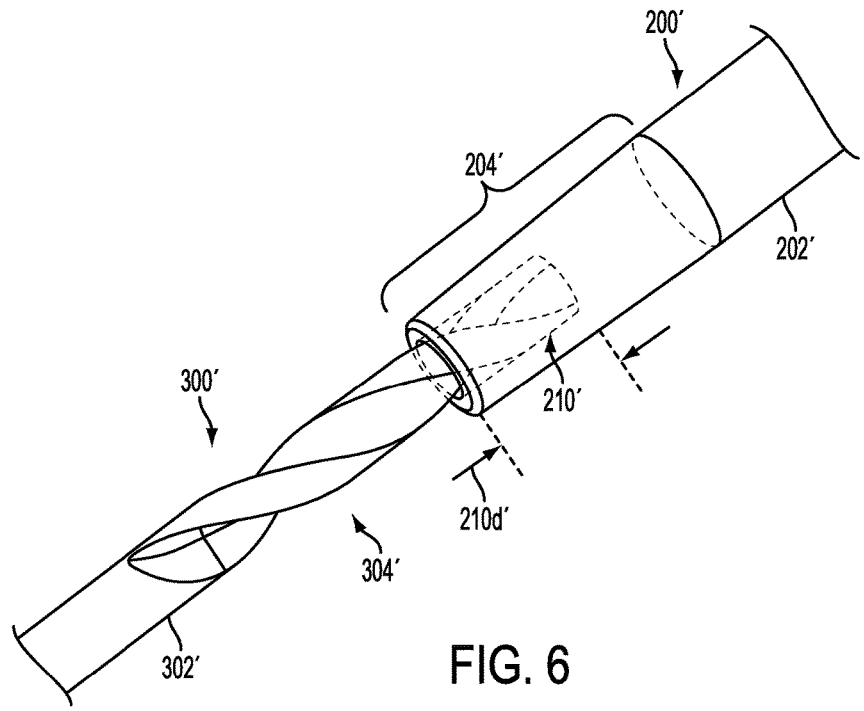
FIG. 6 is a perspective, partially transparent view of another embodiment of a pusher shaft having a portion of one embodiment of a pin seated in a bore formed in the pusher shaft.

FIG. 6 illustrates another exemplary embodiment of a pusher shaft 200'. The pusher shaft 200', also shown in FIG. 10, can generally be configured and used similar to the pusher shaft 200 of FIG. 5. In the illustrated embodiment, the pusher shaft 200' includes a handle 206' having a shaft 202' extending therefrom. The handle 206' in this illustrated embodiment is a solid member, e.g., lacks a cavity formed therein. The shaft 202' has a bore 210' formed therein at an end of the pusher shaft 200' opposite the handle 206'. The bore 210' in this illustrated embodiment is contained fully within a tapered tip portion 204' of the shaft 202' and has a depth 210d' of about 5 mm.

Figure 7:
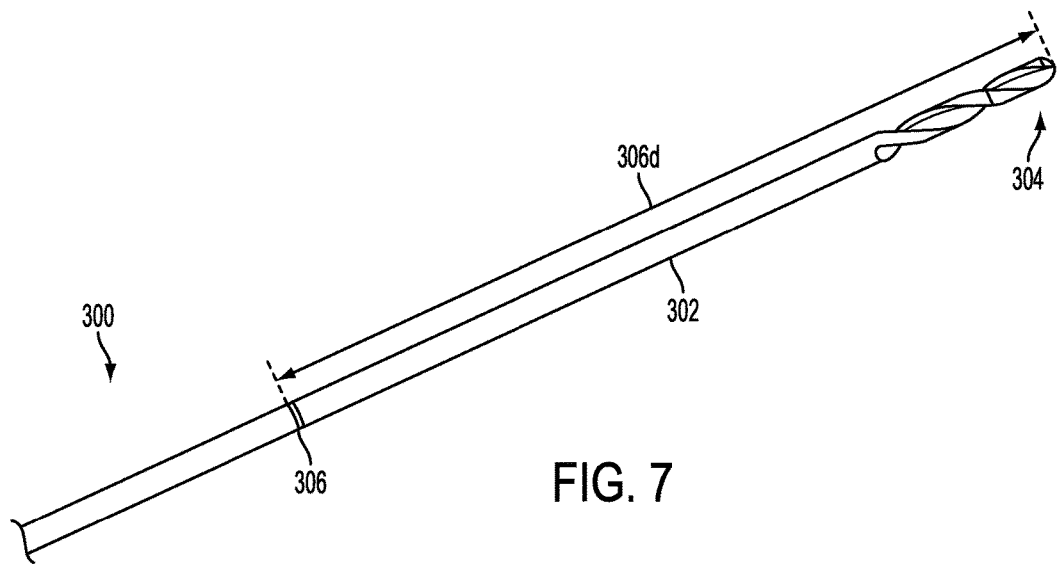
FIG. 7 is a perspective, partial view of one embodiment of a pin.

A pin can have a variety of sizes, shapes, and configurations. FIG. 7 illustrates one exemplary embodiment of a pin 300. The pin 300 can be elongate and can include a shaft 302 having a first end 304 and a second end (not shown). The shaft 302 has a circular cross-sectional shape in the illustrated embodiment, which can facilitate smooth advancement of at least a portion of the shaft 302 through tissue, e.g., through tissue adjacent a bone having a bone tunnel formed therein, and/or through a bone tunnel. However, the shaft 302 can have other cross-sectional shapes, e.g., ovular, octagonal, etc. The shaft 302 can have a constant diameter along a longitudinal length thereof, or, as in the illustrated embodiment, the shaft 302 can have different diameters at various portions along its longitudinal length. The diameter of the pin 300 in an least an intermediate portion thereof between the shaft's first end 304 and second end can be configured to allow the pin to be seated within a passageway of a gauge member in a clearance fit, as discussed further below.

A first end 304 of the shaft 302 can be configured to facilitate penetration of the pin 300 into bone. The pin shaft's first end 304 can be configured to form a bone tunnel in bone and/or to expand a previously formed bone tunnel, as will be appreciated by a person skilled in the art. In the illustrated embodiment, the first end 304 includes a drill bit configured to drill into bone. A second end (not shown) of the shaft 302 opposite the first end 304 can be configured to couple to an implant (not shown) configured to be implanted within a patient's body to facilitate attachment of tissue to bone, such as elongate bar coupled to a loop, e.g., a suture, having a graft looped thereover. In this way, the first end 304 can be configured to be passed through bone, e.g., through a bone tunnel formed in the bone, with the implant coupled to the pin's second end being configured to be pulled into the bone tunnel as the pin 300 passes through the bone tunnel.

The pin 300 can include an indicator mark 306 thereon. In an exemplary embodiment, the pin 300 can include a single indicator mark 306, as in the illustrated embodiment. The indicator mark 306 can have a variety of sizes, shapes, and configurations. The indicator mark 306 can be configured to be visible around an entirety of a circumference or perimeter of the pin 300, which can facilitate visualization of the indicator mark 306 regardless of a vantage point of viewing the pin 300 and/or can facilitate visibility of the indicator mark through a window of a gauge member. In the illustrated embodiment, the indicator mark 306 includes a single circumferential line extending around a circumference of the shaft 302. In other words, the indicator mark 306 in the illustrated embodiment is a ring. Extending around a circumference or perimeter of the shaft 302 can help ensure that the indicator mark 306 is visible through a window of a gauge member, regardless of the pin's rotational orientation relative to the gauge member, when the pin 300 is positioned within a passageway of the gauge member, as discussed further below. The indicator mark 306 is a solid line in the illustrated embodiment, but the line can be dashed, dotted, etc. To facilitate visualization of the indicator mark 306, the indicator mark 306 can be in a bright color, can be configured to fluoresce when exposed to a fluorescent source, and/or can have a color that highly contrasts with a color of the shaft 302. In one embodiment, the indicator mark 306 can have a red color, and the shaft 302 can have a gunmetal gray color such that the indicator mark 306 highly contrasts against the shaft 302.

The indicator mark 306 can be formed on or formed in the pin's shaft 302 at a predetermined location along the longitudinal length of the shaft 302. The predetermined location can be in the intermediate portion of the shaft 302 between the shaft's first end 304 and second end at a distance 306d from a terminal tip of the shaft 302 at the first end 304. The indicator mark 306 can be positioned near the first end 304 of the shaft 302, as shown in the illustrated embodiment. Being positioned near the first end 304 can facilitate visualization of the indicator mark 306 through one or more windows of a gauge member and/or can help ensure that the indicator mark 306 is disposed within a patient's body when the first end 304 of the shaft 302 and the second end of the shaft 302 are each positioned outside a bone and the intermediate portion of the shaft 302 is at least partially disposed within the bone, as discussed further below. The distance 306d can be based on a typical depth of a bone in which the pin can be configured to be inserted. The distance 306d can be greater than the bone's typical depth, which can help ensure that the indicator mark 306 is positioned outside the bone when the pin 300 is advanced therethrough with opposed ends extending outwardly from opposed sides of the bone. The distance 306d can have a variety of values. In an exemplary embodiment, the distance 306d can be based on a typical depth of a femur and can be up to about 8 in (203.2 mm), e.g., up to about 200 mm, about 68 mm, about 75 mm, in a range of about 68 mm to 75 mm, in a range of about 68 mm to 203.2 mm, in a range of about 3 in (76.2 mm) to 8 in, in a range of about 75 mm to 200 mm, etc.

At least a portion of the first end 304, e.g., at least a portion of the drill bit, can be configured to be seated within a bore of a pusher shaft. At least the portion of the first end 304 being seated within the bore can facilitate proper positioning of the indicator mark 306 within one or more windows of a gauge member, as discussed further below. In an exemplary embodiment, a pin can be configured to abut an end of a pusher shaft's bore within the pusher shaft, which can facilitate predictable relative positioning of the pusher shaft and the pin's indicator mark.

As in the illustrated embodiment, the pin 300 can be a solid, rigid member. Alternatively, the pin 300 can have one or more hollow portions therein and/or can have at least one flexible portion. In an exemplary embodiment, at least a portion of the pin 300 including the indicator mark 306 and the first end 304 configured to penetrate into bone can be rigid.

Figure 8:
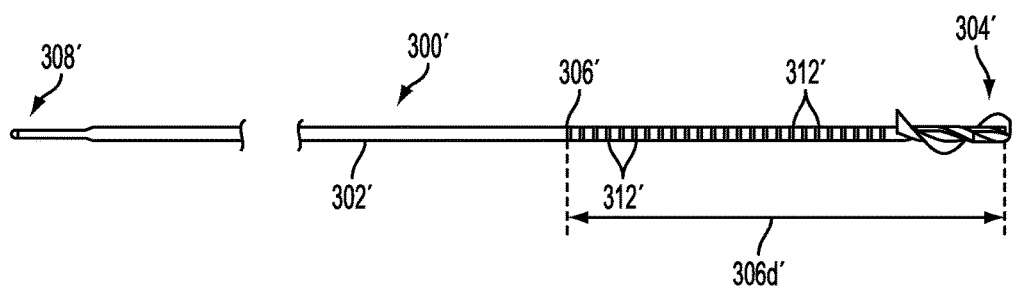
FIG. 8 is a side view of the pin of FIG. 6.
Figure 12:
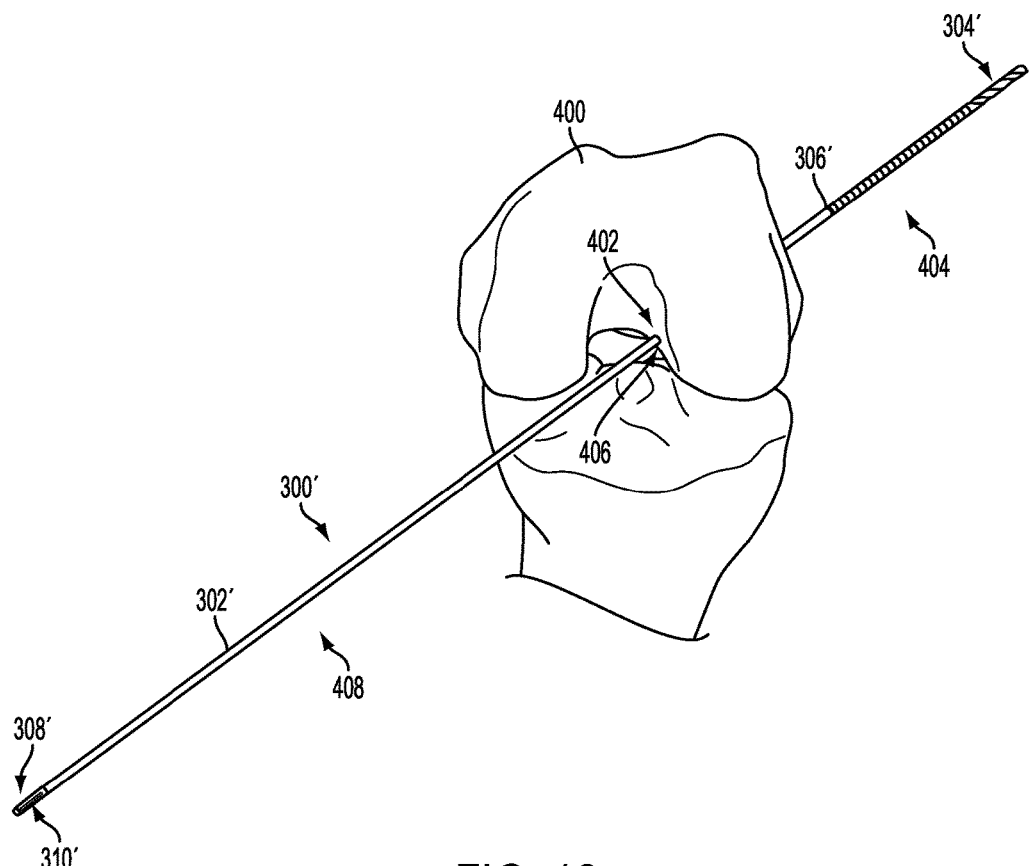
FIG. 12 is a perspective view of the pin of FIG. 8 extending through a bone tunnel formed in a femur with a first portion of the pin positioned outside the femur on one side of the femur and with a second portion of the pin positioned outside the femur on an opposite side of the femur.

FIGS. 6 and 8 illustrate another exemplary embodiment of a pin 300'. The pin 300', also shown in FIG. 12, can generally be configured and used similar to the pin 300 of FIG. 7. In the illustrated embodiment, the pin 300' includes a shaft 302' having a first end 304' configured to facilitate penetration of the pin 300' into bone, and having a second, opposite end 308' configured to couple to an implant (not shown). The first end 304' includes a drill bit, and the second end 308' has an opening 310' formed therein, as shown in FIG. 12. The opening 310' can be configured to facilitate coupling of an implant to the pin 300', e.g., by passing a loop of the implant through the opening 310'. The first end 304' can be configured to be seated within a bore formed in a pusher shaft, such as the bore 210' of the pusher shaft 200', as shown in FIG. 6. The pin 300' can abut an end of the bore 210', as shown in FIG. 6. The pin 300' abutting the end of the bore 210' can be palpably felt when the pin 300' is advanced into the bore 210'. The shaft 302' has an indicator mark 306' formed thereon, which in the illustrated embodiment is at a distance 306d' of about 68 mm from a terminal tip of the shaft 302' between a tip of the shaft 302' at the shaft's first end 304'.

The pin 300' can include one or more depth markings 312' formed on or formed in the shaft 302'. The one or more depth markings 312' can be configured to indicate a depth, e.g., a drill depth, of the pin 300' when the pin 300' is advanced, e.g., drilled, into bone. The pin 300' includes twenty-four depth markings 312' in the illustrated embodiment, but the pin 300' can include any number of the depth markings 312'.

In another exemplary embodiment, a pin can include an indicator mark in the form of at least one protrusion extending radially outward therefrom. The at least one protrusion can generally be configured and used similar to the indicator mark 306 of FIG. 7. The at least one protrusion can be configured to be positioned within and extend through a gauge member's window so to be at least partially positioned outside the gauge member's passageway. The at least one protrusion can be configured to slide within the window as the gauge member is slid relative to the pin with the pin positioned within the gauge member's passageway. For example, the at least one protrusion can be configured to be positioned within and slide within the window 112x of the gauge member 100x of FIG. 1A. The protrusion's position within a window of a gauge member can be determined relative to the gauge member's indicia similar to that discussed above.

Figure 8A:
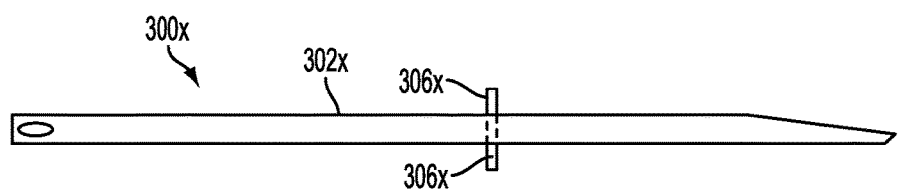
FIG. 8A is a side view of another embodiment of a pin.
Figure 8B:
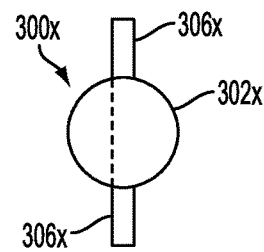
FIG. 8B is an end view of the pin of FIG. 8A.

FIGS. 8A and 8B illustrate one embodiment of a pin 300x having an indicator mark 306x in the form of at least one protrusion extending radially outward from a shaft 302x of the pin 300x. The pin 300x can generally be configured and used similar to the pin 300 of FIG. 7. The at least one protrusion can have a variety of sizes, shapes, and configurations. As in the illustrated embodiment, the at least one protrusion 306x can include a crosspin extending radially outward from the pin 300x. The at least one protrusion 306x in the illustrated embodiment is formed as a single element that extends through the pin to have opposed ends thereof positioned on either side of the pin's shaft. The opposed ends can be configured to simultaneously extend through opposed windows formed in a gauge member. However, a pin can have any number of protrusions. The number of protrusions can equal a number of windows in a gauge member in which the pin is configured to be positioned within. If a pin includes a plurality of protrusions as in the illustrated embodiment which includes two protrusions, any two or more of the protrusions can be formed as a singular element, or each of the protrusions can be discrete element. For example, each of the protrusions can be a singular element that extends radially outward from a sidewall of the pin's shaft.

Figure 9:
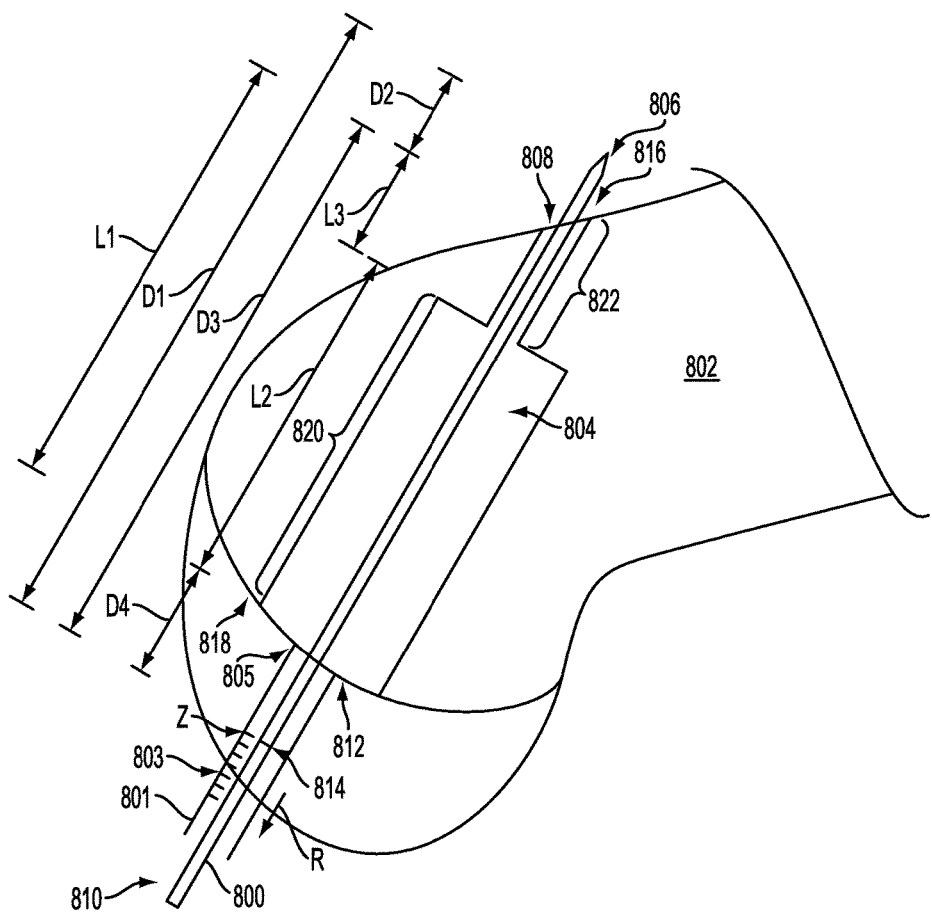
FIG. 9 is a schematic view of an embodiment of a pin extending through a bone tunnel formed in a femur.
Figures 10, 11:
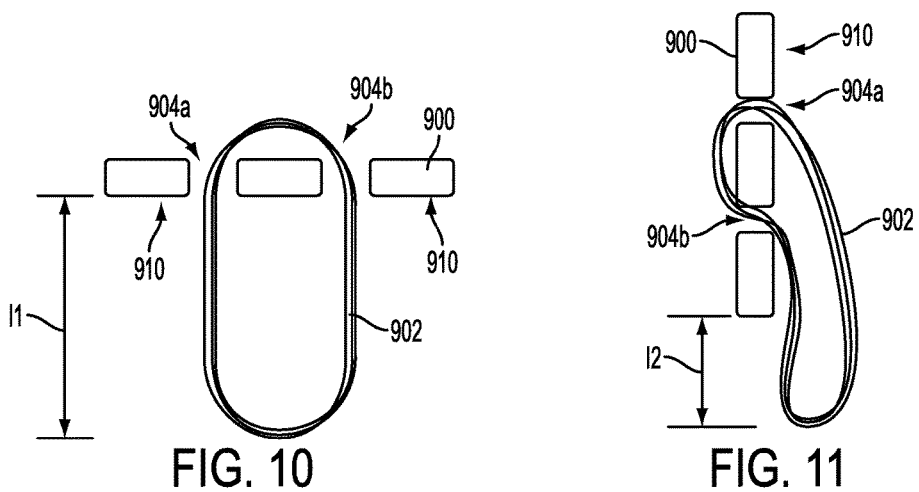
FIG. 10 is a schematic side, cross-sectional view of an embodiment of an implant including an elongate bar having a loop coupled thereto, the implant being in a deployed configuration.
FIG. 11 is a schematic side, cross-sectional view of the implant of FIG. 10 in a deployment configuration.

FIGS. 9-11 demonstrate an exemplary embodiment of a method for determining the location and value(s) of one or more indicia be used on a gauge member to provide one or more characteristics related to a bone tunnel. A bone 802 having a bone tunnel 804 formed therein is shown in FIG. 9 for ease of explanation and are not needed for calibration, e.g., they are not needed to determine the location and reference values for indicia on a gauge member. For ease of explanation, a gauge member 801 is illustrated having a single scale 803 for indicia, but as mentioned above, a gauge member can include other indicia. Additionally, the bone 802 of FIG. 9 is a femur, but as mentioned above, pins, gauge members, and pusher shafts discussed herein can be used with a variety of different bones.

A first distance D1, shown in FIG. 9, between an insertion end 806 of a pin 800 and an indicator mark 814 formed on the pin 800 can be a known distance because the indicator mark 814 can be at a predetermined location on the pin 800, as discussed above. A second distance D2, can also be known because a known length of the pin 800 can be disposed within a bore of a pusher shaft (not shown), as defined by a depth of the bore, as also discussed above. When the pusher shaft (not shown) is abutted against bone, e.g., against a first surface 816 thereof, the second distance D2 can also correspond to a distance from the insertion end 806 of the pin 800 of the first surface 816 of the bone 802. A third distance D3 between the first surface 816 of the bone 802 and the indicator mark 814 can thus be known as the first distance D1 minus the second distance D2, i.e., D3=(D1−D2).

The known first, second, and third distances D1, D2, D3 can be used in addition to one or more known values related to the gauge member 801 to determine the location and value(s) of one or more indicia to be located on the gauge member 801 to form the scale 803. For example, if it is desired to have the scale 803 indicate a total bone tunnel length L1 of the tunnel 804, a zero reference mark Z can be formed on the gauge member 801 nearest the gauge member's insertion end 805. The zero reference mark Z can have a value equal to the third distance D3 minus a fourth distance D4 that is defined by a distance between the gauge member's insertion end 805 and a position of the zero mark Z along the guide member's longitudinal length. The values of the scale's marks, regardless of the characteristic being indicate by the scale 803, can decrease in a direction away from the gauge member's insertion end 805, e.g., decrease in a direction of arrow R, such as the zero mark Z being 50 mm and each subsequent mark in the direction R decreasing by 2 mm. The actual distance between each subsequent mark would like be 2 mm. In use, the socket portion 820 may not yet be formed, as shown in FIG. 9, thus allowing the gauge member 801 to be advanced over the pin 800 to abut against the bone 802 and indicate one or more characteristics related to the bone tunnel 804.

The known first, second, and third distances D1, D2, D3 can be used in addition to one or more known values related to a specific implant size to determine a location and value(s) of a gauge member's indicia. FIGS. 10 and 11 illustrate an embodiment of an implant including an elongate bar 900 (shown in cross-section) and a loop 902 coupled to the bar 900 via holes 904*a*, 904*b* formed in the bar 900. FIG. 10 shows the bar 900 and the loop 902 when the implant is in a deployed configuration, e.g., in a configuration in which a surface 910 of the bar 900 is configured to abut the first surface 816 of the bone 802 and the loop 902 is configured to extend into the bone tunnel 804, e.g., into a reduced diameter portion 822 of the tunnel 804. In the deployed configuration, a first length I1 of the loop 902 extends from the bar 900. The first length I1 can be a known value based on a size of the implant. FIG. 11 shows the bar 900 and the loop 902 when the implant is in a deployment configuration, e.g., in a configuration in which the bar 900 and the loop 902 are configured to pass through the tunnel 804. In the deployment configuration, a second length I2 of the loop 902 extends from the bar 900. The second length I2 can also be a known value based on the size of the implant. A difference between the first length I1 and the second length I2 (I1–I2) can thus be known and can generally define an amount of distance I3, referred to herein as a predetermined distance I3 (not labeled), e.g., in a range of about 2 to 10 mm, needed to rotate the implant outside of the bone 802 from the deployment configuration to the deployed configuration.

The loop 902 can be configured to have a graft (not shown) coupled thereto, as will be appreciated by a person skilled in the art. The loop 902 can be configured to extend into the bone tunnel 804 so as to position the graft within the bone tunnel 804. As will be appreciated by a person skilled in the art, the graft is typically positioned within a socket portion 820 of the tunnel 804, and the loop is typically positioned within the reduced diameter portion 822 of the tunnel 804 which has a diameter that is smaller than a diameter of the socket portion 820. The first length I1 can define a desired length L3 of the reduced diameter portion 822. In other words, the gauge member 801 can be configured to indicate a length of the socket portion 820 to be formed so as to cause the reduced diameter portion 822 to have a length L3 that corresponds to the first length I1.

The known first, second, and third distances D1, D2, D3 can be used in addition to the known first length I1 to calibrate the gauge member's scale 803 for an implant having a specific size. For example, if the scale 803 is going to indicate a total depth L2 of the socket portion 820 to be formed in the bone 802, the zero mark Z can have a value equal to the third distance D3 minus the fourth distance D4 and minus the first length I1. As discussed further below, the position of the indicator mark 804 along the scale will indicate the total depth of the socket portion 820 for a specific implant size. If the indicator mark 814 falls outside of the scale 803, a scale for a differently sized implant can be compared to the indicator mark 814 to determine the appropriate socket depth L2 for that sized implant. For another example, if it is desired to have a scale 803 that indicates GT interface depth, the zero mark Z can have a value equal to the third distance D3 minus the fourth distance D4, minus the first length I1, and minus the predetermined distance I3. The predetermined distance I3 can, as discussed above, reflect allow the implant to be moved between the deployment and deployed configuration.

The pins, pusher shafts, and gauge members discussed herein can each be formed from a variety of materials. Examples of materials that can form any one or more of the pins, pusher shafts, and gauge members, alone or in any combination, including polymers (e.g., polyetheretherketone (PEEK), polylactic acid (PLA), etc.) and metals (e.g., stainless steel, titanium, etc.). Each of the pins, pusher shafts, and gauge members can be formed of same material(s) or be formed of different material(s). In an exemplary embodiment, each of the pins, pusher shafts, and gauge members can be formed of one or more biocompatible rigid materials, e.g., one or more metals, which can help prevent the pins, pusher shafts, and gauge members from deforming or flexing when inserted into a patient's body. This lacks of deformation or flexing can facilitate accurate positioning of the pin's indicator mark relative to the gauge member, as discussed further below.

A surgical kit can be provided including one or more pins, one or more pusher shafts, and one or more gauge members. Each of the gauge members can have a different combination of one or more scales thereon, e.g., a first gauge member having a scale thereon for an implants of size "A" and a scale thereon for an implants of size "B," a second gauge member having a scale thereon for an implants of size "C" and a scale thereon for an implants of size "D," a third gauge member having a scale thereon for an implants of size "A" and a scale thereon for an implants of size "E," etc. Each of the pins can have a different size, different shape, and/or different configuration than the other pins, each of the pusher shafts can have a different size, different shape, and/or different configuration than the other pusher shafts, and each of the gauge members can have a different size, different shape, and/or different configuration than the other gauge members. In this way, the pin having the most appropriate size, shape, and configuration, the pusher shaft having the most appropriate size, shape, and configuration, and the gauge member having the most appropriate size, shape, and configuration can be selected for use in a particular surgical procedure with a particular patient, which can help a single kit accommodate different situations, such as different surgical procedures, different patient anatomies, various implant sizes, and various graft sizes. The kit can optionally include one or more implants. Each of the implants can have a different size, different shape, and/or different configuration than the other implants. In an exemplary embodiment, each of the implants can have a size corresponding to a scale on at least one of the gauge members included in the kit. For each different scale on the one or more gauge members, the kit can include can include at least one implant having a size that corresponds thereto. The kit can optionally include one or more additional surgical tools configured to be used in a same surgical procedure as the one or more pins, the one or more pusher shafts, and the one or more gauge members, e.g., one or more drills each configured to form a bone tunnel, one or more sutures configured to engage a graft and/or an implant, one or more grafts (e.g., artificial grafts of different sizes, etc.), one or more sutures configured to couple an implant and a graft together, etc.

In use, as mentioned above, the pins, pusher shafts, and gauge members discussed herein can be used in a minimally invasive surgical procedure for securing a soft tissue to bone. Generally, the patient can first be prepared for the surgery using standard techniques.

FIGS. 12-19 illustrate an exemplary embodiment of a surgical procedure for soft tissue repair. Although the procedure is illustrated with respect to the gauge member 100' of FIGS. 3 and 4, the pusher shaft 200' of FIG. 6, and the pin 300' of FIGS. 6 and 8, any of the gauge members, pusher shafts, and pins disclosed herein can be similarly used. Also, although the procedure is illustrated with respect to ACL repair, the gauge members, pusher shafts, and pins disclosed herein can be used to surgically repair various problems.

As shown in FIG. 12, the pin 300' can be advanced through a femur 400 of a patient. The pin 300' can be advanced therethrough in a variety of ways, as will be appreciated by a person skilled in the art, such as by drilling the pin 300' through the femur 400. The pin 300' can be advanced through a bone tunnel 402 previously formed in the femur 400, or advancement of the pin 300' through the femur 400 can form the bone tunnel 402. As in the illustrated embodiment, the bone tunnel 402 can be an anterior medial (AM) tunnel. A trajectory of the bone tunnel 402 through the femur 400 can be based on any number of factors, e.g., patient anatomy, as will be appreciated by a person skilled in the art.

The pin 300' can be positioned within the bone tunnel 402 such that a first portion 408 of the pin 300' extends out a first end 410 (shown in FIGS. 14 and 15) of the bone tunnel 402 and is positioned outside the femur 400, such that a second portion 404 of the pin 300' extends out a second end 406 of the bone tunnel 402 and is positioned outside the femur 400 on an opposite side from the first portion 404, and such that an intermediate portion (not shown) of the pin 300' between the first and second portions 408, 404 is disposed within the femur 400 in the bone tunnel 402. The first and second portions 408, 408 of the pin 300' can be positioned outside the femur 400 but be at least partially disposed within the patient's body, e.g., in tissue (not shown) surrounding the femur 400. The first and second portions 408, 404 of the pin 300' can each have any longitudinal length, same or different from one another. In an exemplary embodiment, the first portion 408 can have a longitudinal length equal to or greater than the distance 306d' between the indicator mark 306' and the pin's tip at the first end 304'. In other words, as shown in FIG. 12, when the pin 300' extends through the bone tunnel 402, the indicator mark 306' can be positioned outside the femur 400. In other words, the indicator mark 306' can enter the femur 400 through the second end 406 of the bone tunnel 402, move through the bone tunnel 402, and exit the femur 400 through the first end 410 of the bone tunnel 402 so as to be positioned outside the femur 400. Positioning the indicator mark 306' outside the femur 400 can help ensure that an adequate amount of the pin 300' is positioned outside the femur 400 to facilitate coupling of the pusher shaft 200' and the gauge member 100' to the first and second portions 408, 404 pin 300', as discussed further below.

Figure 13:
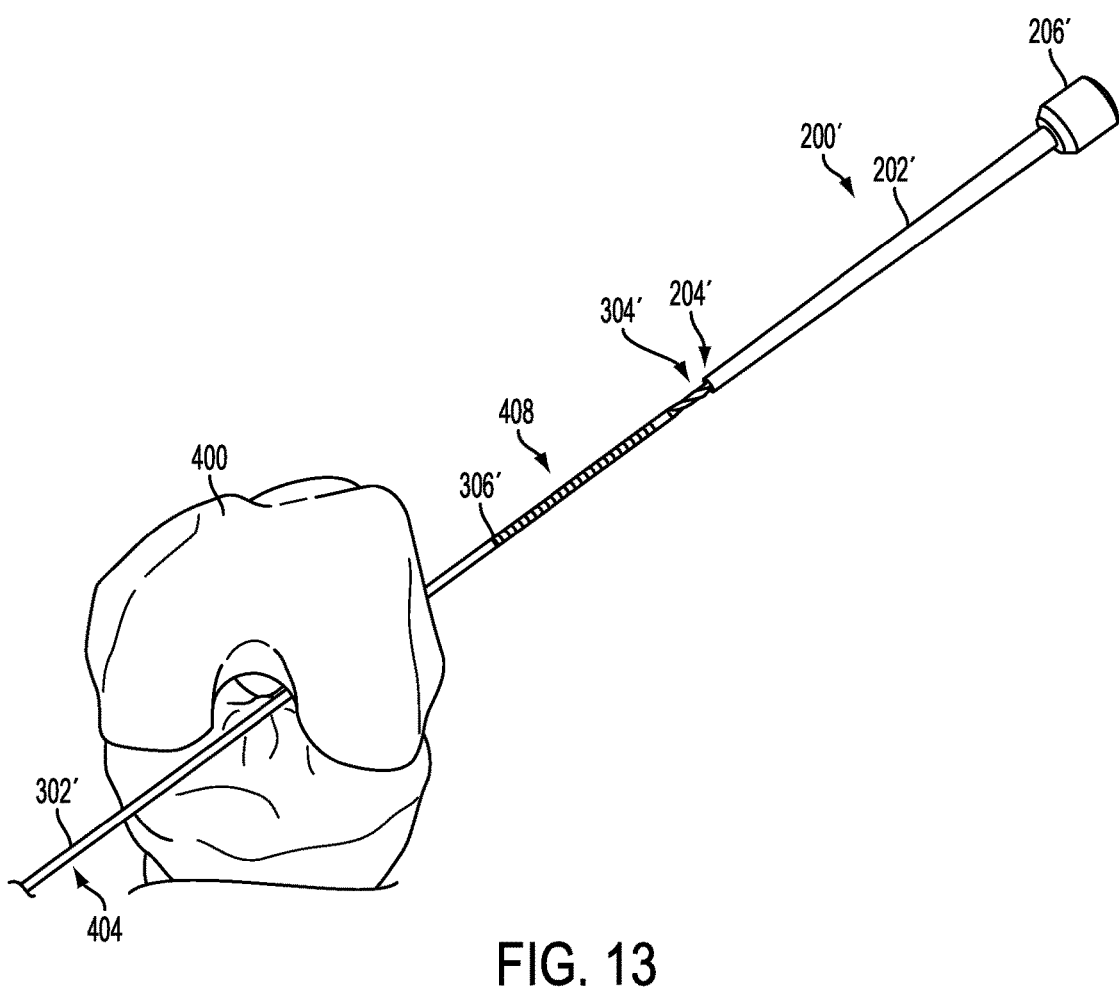
FIG. 13 is a perspective view of at least some of the first portion of the pin of FIG. 9 seated in the bore of the pusher shaft of FIG. 6.

The pin 300' extending through the femur 400 can be coupled to the pusher shaft 200'. The first end 304' of the pin 300' positioned outside of the femur 400 can be seated in the bore 210' at the tip portion 204' of the pusher shaft 200', as shown in FIG. 13. The first end 304' and the bore 210' can be sized such that the first end 304' has a clearance fit within the bore 210', as shown in FIG. 6. The clearance fit can facilitate a positive hold between the pin 300' and the pusher shaft 200', thereby helping to maintain the pin 300' and the pusher shaft 200' in a fixed, predictable position relative to one another. The positive hold and/or fixed, predictable positioning can, e.g., facilitate smooth, predictable pushing of the pin 200' with the pusher shaft 300'.

Figure 14:
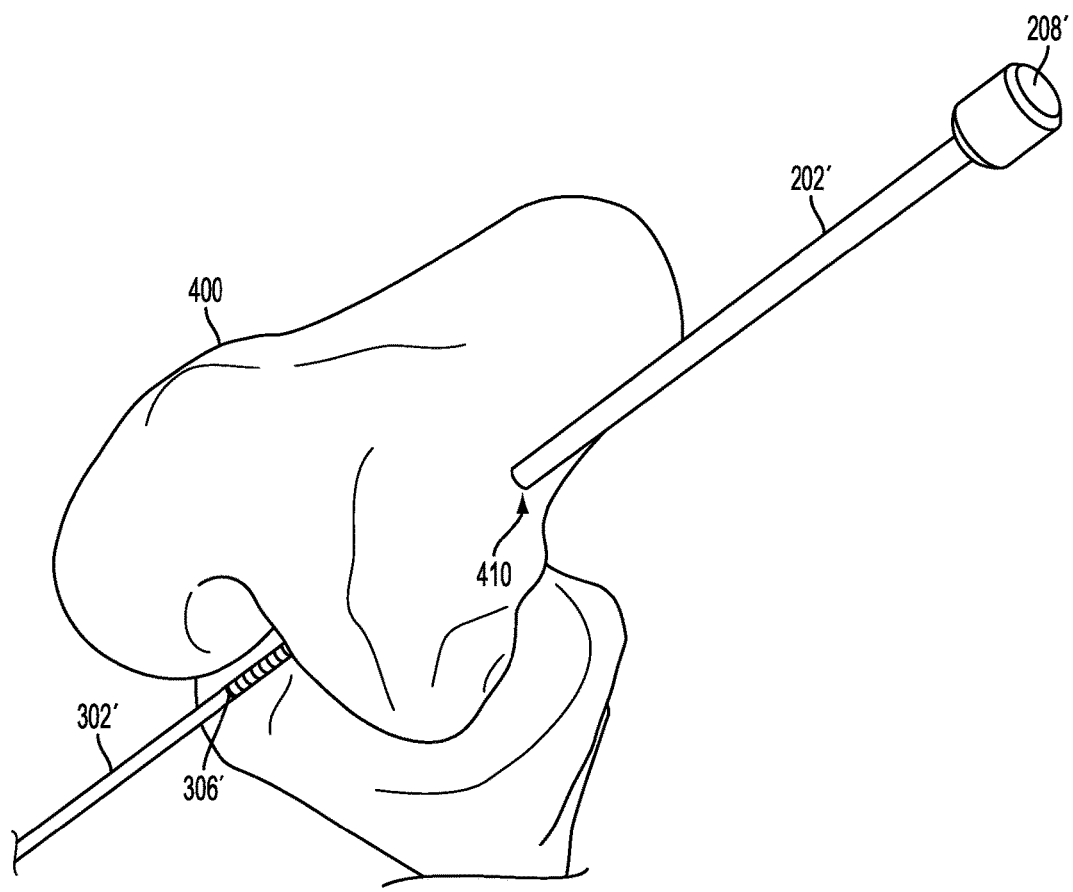
FIG. 14 is a perspective view of the pusher shaft of FIG. 13 with the pusher shaft abutting the femur.
Figure 15:
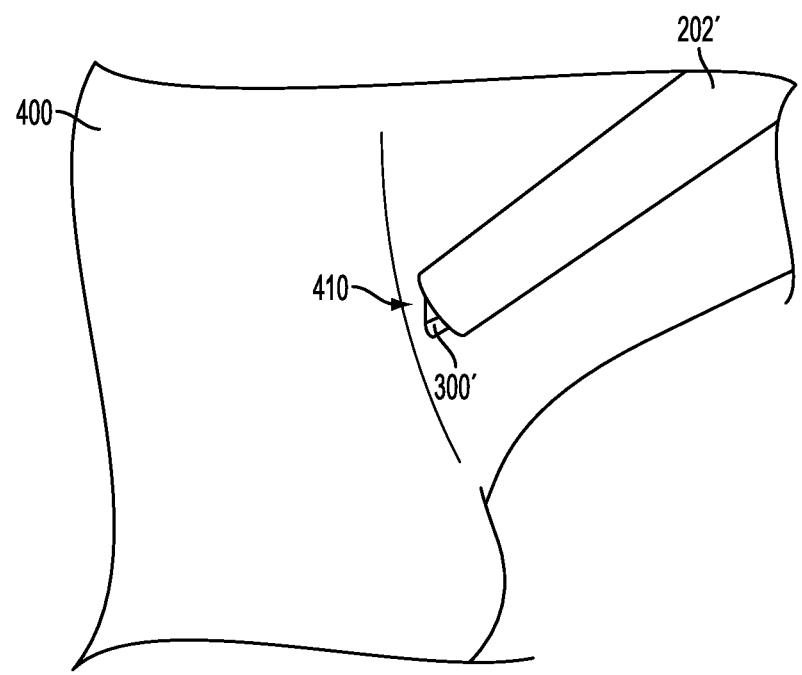
FIG. 15 is another perspective view of the pusher shaft of FIG. 13 with the pusher shaft abutting the femur.

When the first end 304' of the pin 300' is seated in the pusher shaft's bore 210', or is otherwise coupled to the pusher shaft 210', the pusher shaft 200' can be pushed relative to the femur 400 in a direction toward the femur 400 so as to push the pin 300' through the bone tunnel 402 in a direction toward the bone tunnel's second end 406. The pusher shaft 200' can be pushed in any one or more ways, e.g., pushed by hand on the flat or planar end 208', hit with a mallet, pushed via a driver inserted into the pusher shaft's cavity 206c, etc. The pin 300' can thus be caused to pass through the bone tunnel 402 in a direction opposite to a direction in which the pin 300' was previously advanced therethrough, e.g., when the pin's first end 304' led the pin 300' through the femur 400. The pusher shaft 200', and hence also the pin 300', can be pushed relative to the femur 400 until the pusher shaft 200' abuts a surface of the femur 400, as shown in FIGS. 14 and 15. The pusher shaft 200' can abut the femur 400 adjacent the bone tunnel's first end 410 because, when the pusher shaft 200' and the pin 300' are collectively pushed toward the femur 400, the pin 300' extends through the bone tunnel 402 and the pusher shaft 200' is coupled to the pin 300' on a side of the femur 400 facing the bone tunnel's first end 410. In other words, the pusher shaft 200' and the pin 300' can be pushed until the pusher shaft 200' directly contacts the femur 400. As mentioned above, the pusher shaft 200' can have a diameter larger than the pin's diameter and larger than the bone tunnel's diameter such that the pin 300' can pass through the tunnel 402 but the pusher shaft 200' cannot pass through the bone tunnel 402. When the pusher shaft 200' abuts the femur's surface, the pusher shaft 200' may or may not rest flush against the surface of the femur 400 depending on, e.g., a topography of the femur's surface. In the illustrated embodiment, the pusher shaft 200' does not rest flush against the femur 400, as shown in FIG. 15. The pusher shaft 200' abutting the femur 400 can be palpably detected by a user of the pusher shaft 200', e.g., because the pusher shaft 200' can no longer be pushed toward the second end 406 of the bone tunnel 402. However, the pusher shaft 200' abutting the femur 400 can additionally or alternatively be visually confirmed, e.g., using an minimally invasive camera, an arthroscope, and/or other visualization device, as will be appreciated by a person skilled in the art.

Figure 16:
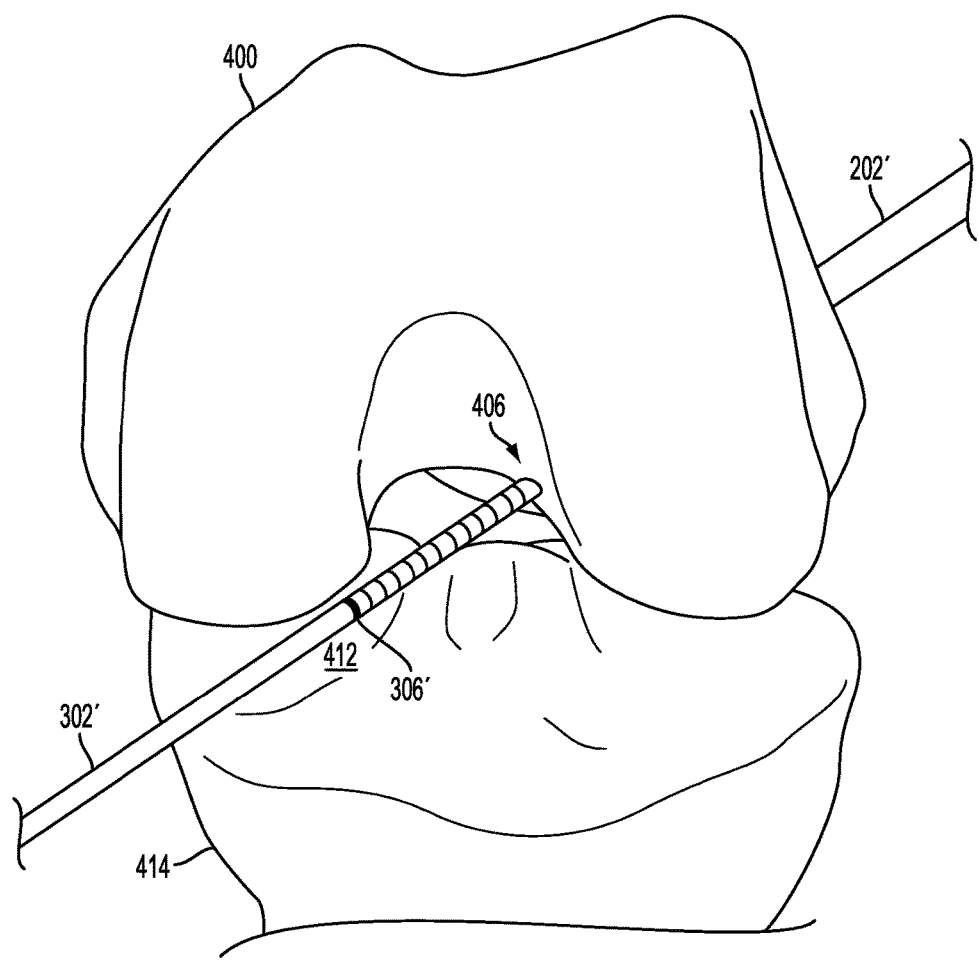
FIG. 16 is yet another perspective view of the pusher shaft of FIG. 13 with the pusher shaft abutting the femur.

Pushing the pin 300' through the bone tunnel 402 can cause the indicator mark 306' to be pushed farther away from the second end 406 of the bone tunnel 402, as shown in FIG. 16. The indicator mark 306' can thus be advanced through each of the first and second ends 410, 406 of the bone tunnel 402 for a second time. In other words, the indicator mark 306' can reenter the femur 400 through the first end 410 of the bone tunnel 402, move through the bone tunnel 402, and exit the femur 400 for a second time through the second end 406 of the bone tunnel 402 so as to again be positioned outside the femur 400. The indicator mark 306' can, however, be positioned relative to the femur 400 in other ways depending on, e.g., a size of the femur 400 and on a longitudinal length of the pin 300'. For example, the indicator mark 306' can be positioned within the bone tunnel 402 or outward of the tunnel's second end 406 when the pusher shaft 200' is coupled to the pin's first end 304' and when the pusher shaft 200' and the pin 300' are pushed relative to the femur 400.

As shown in FIG. 16, when the pusher shaft 200' abuts the femur 400, the indicator mark 306' can be positioned in an intra-articular space 412 between the femur 400 and a tibia

414. In other words, when the pusher shaft 200' abuts the femur 400, the indicator mark 306' can be within the intra-articular space 412 on the side of the femur 400 having the second end 406 of the bone tunnel 402 formed therein. A position of the indicator mark 306' within the intra-articular space can be visually verified, e.g., using a minimally invasive camera, an arthroscope, and/or other visualization device, as will be appreciated by a person skilled in the art.

Figure 17:
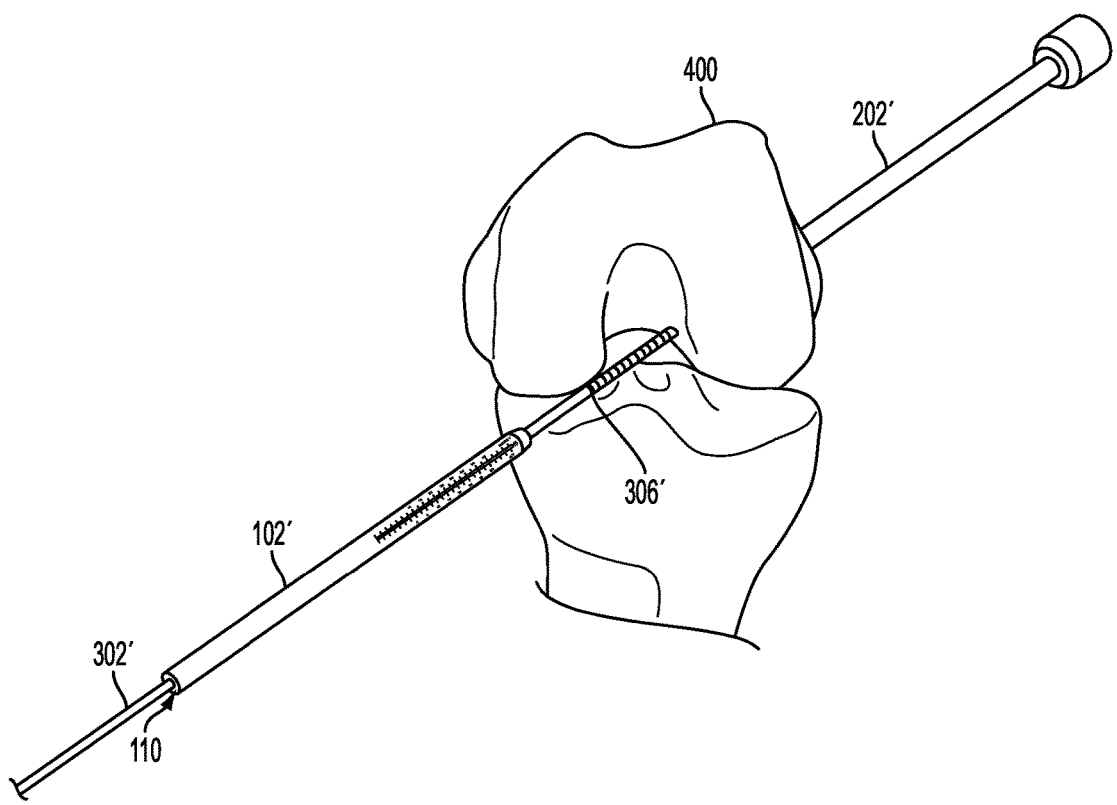
FIG. 17 is a perspective view of the pin and the pusher shaft of FIG. 13 with at least some of the second portion of the pin being positioned within a passageway extending through the gauge member of FIG. 3.

The pin 300' extending through the femur 400 can be coupled to the gauge member 100' by positioning the pin 300' within the passageway 110' of the gauge member 100', as shown in FIG. 17. The pin 300' can be positioned within the passageway 110' of the gauge member 100' by sliding the gauge member 100' over the pin 300'. The gauge member 100' can be coupled to the pin 300' such that a first end 104' of the gauge member 100', shown in FIGS. 3 and 4, is positioned closer to the femur 400 than a second end 106' of the gauge member 100'. In other words, the window 112' adjacent the first end 104' and an end portion 108' of the shaft 102' adjacent the first end 104' can be positioned closer to the femur 400 than the second end 106' of the gauge member 100'. The passageway 110' and the pin 300' can be sized such that the pin 300', e.g., the pin's shaft 302', has a clearance fit within the passageway 110'. The clearance fit can facilitate a positive hold between the pin 300' and the gauge member 100', thereby helping to maintain the gauge member 100' in a fixed, predictable position relative to the pin 300' and to the femur 400. The positive hold and/or fixed, predictable positioning can, e.g., facilitate smooth, predictable movement of the gauge member 100' when the gauge member 100' is coupled to the pin 300' by having the pin 300' seated in the gauge member's passageway 110'. In an exemplary embodiment, the gauge member 100' can be coupled to the pin 300' after the pusher shaft 200' has been coupled to the pin 300' and after the pusher shaft 200' has pushed the pin 300' through the bone tunnel 402. This can facilitate handling and/or visualization of the second portion 404 of the pin 300' extending out the second end 406 of the bone tunnel 402. The gauge member 100' can, however, be coupled to the pin 300' before the pusher shaft 200' has been coupled to the pin 300' and/or before the pusher shaft 200' has pushed the pin 300' through the bone tunnel 402.

Figure 18:
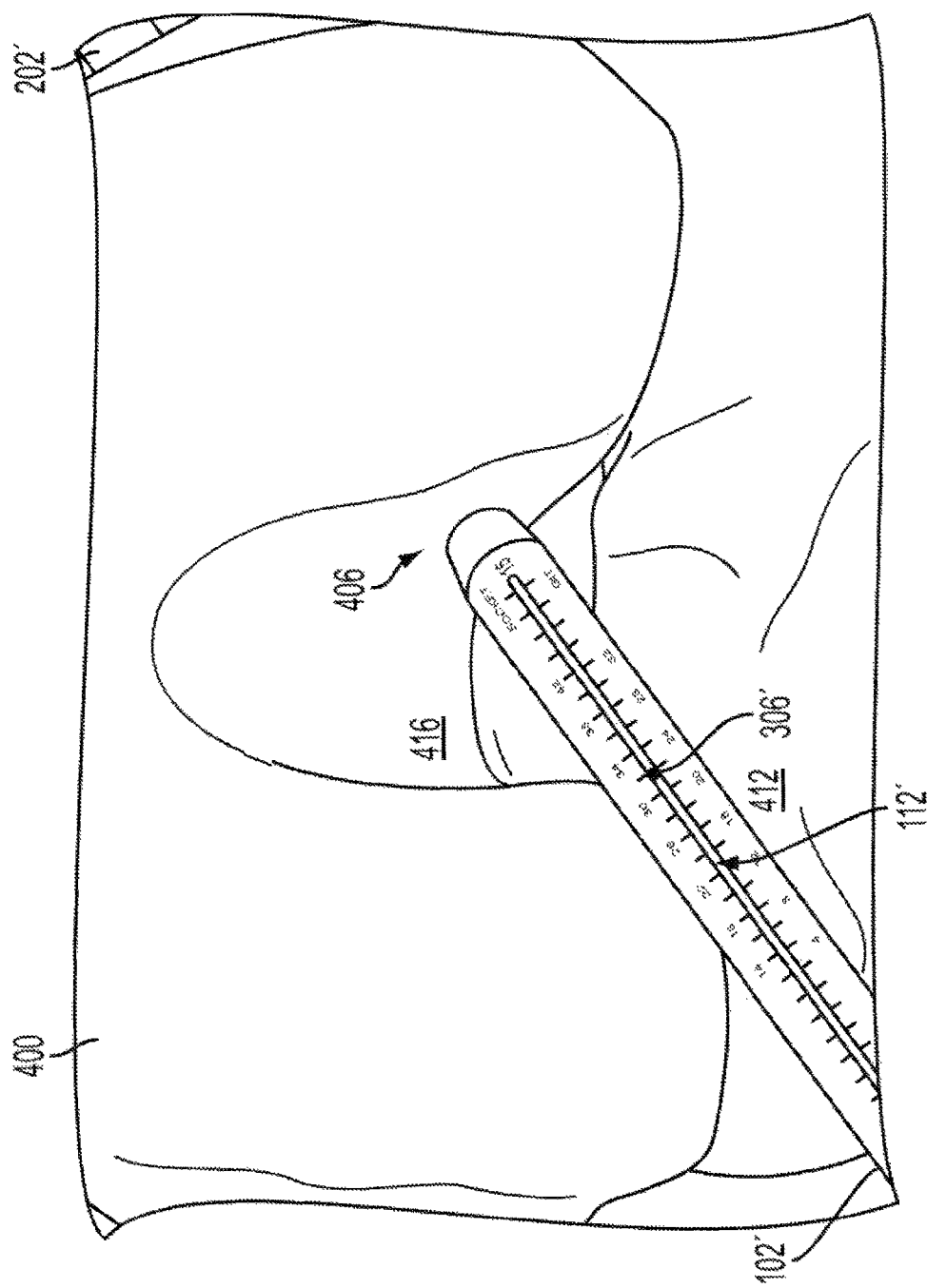
FIG. 18 is a perspective view of the gauge member of FIG. 17 with the gauge member abutting the femur.

The gauge member 100', having the pin 300' seated in the gauge member's passageway 110', can be slidably advanced toward the femur 400 relative to the pin 300'. In other words, the gauge member 100' can be slid over and relative to the pin 300'. The gauge member 100' can be so advanced in any one or more ways, e.g., pushed by hand, pushed via a driver abutting an end of the gauge member 100', etc. The gauge member 100' can be moved relative to the femur 400 and the pin 300' until the gauge member 100' abuts a surface of the femur 400, as shown in FIG. 18. The gauge member 100' can abut the femur 400 adjacent the bone tunnel's second end 406 because, when the gauge member 100' is advanced toward the femur 400, the pin 300' extends through the bone tunnel 402 and the gauge member 100' is coupled to the pin 300' on a side of the femur 400 facing the bone tunnel's second end 406. In other words, the gauge member 100' can be advanced until the gauge member 100' directly contacts the femur 400. As mentioned above, the gauge member 100' can have a diameter larger than the pin's diameter and larger than the bone tunnel's diameter such that the pin 300' can pass through the tunnel 402 but the gauge member 100' cannot pass through the bone tunnel 402. When the gauge member 100' abuts the femur's surface, the gauge member 100' may or may not rest flush against the surface of the femur 400 depending on, e.g., a topography of the femur's surface. In the illustrated embodiment, the pusher shaft 200' does rest flush against the femur 400, as shown in FIG. 18. The gauge member 100' abutting the femur 400 can be palpably detected by a user of the gauge member 100', e.g., because the gauge member 100' can no longer be pushed toward the first end 410 of the bone tunnel 402. However, the gauge member 100' abutting the femur 400 can additionally or alternatively be visually confirmed, e.g., using an minimally invasive camera an arthroscope, and/or other visualization device, as will be appreciated by a person skilled in the art.

The gauge member 100' being advanced toward the femur 400 until the gauge member 100' abuts the femur 400 can cause the gauge member 100' to enter the intra-articular space 412 and an intercondylar notch 416, as shown in FIGS. 18 and 19. The indicator mark 306' positioned within the intra-articular space 412 can thus be positioned within the gauge member's passageway 110' when the pusher shaft 200' is coupled to the pin 300' and the pusher shaft 200' abuts the femur 400. The indicator mark 306' can be positioned within the passageway 110' adjacent the window 112', as also shown in FIGS. 18 and 19. The indicator mark's position relative to the first and second scales 116a', 116b' adjacent the window 112' can thus be determined. The indicator mark 306', the first scale 116a', and/or the second scale 116b' can be relatively small and difficult to visualize in their actual sizes. However, the indicator mark 306', the first scale 116a', and the second scale 116b' can be magnified within the patient's body, e.g., using an minimally invasive camera an arthroscope, and/or other visualization device, as will be appreciated by a person skilled in the art.

The indicator mark 306' being out of range of the first scale 116a' and/or the second scale 116b', can indicate that the implant size, e.g., as indicated by the indicator mark 118', is inappropriate for use with the patient. The pin 300' can be removed from the gauge member's passageway 110', e.g., the gauge member 100' can be removed from the patient's body, and another gauge member (not shown) can be advanced over the pin 300' toward the femur such that the indicator mark 306' is within range of one or more scales of the other gauge member. If a gauge member has a plurality of windows, and the indicator mark 306' is out of range of one of the window's scales, the gauge member can be rotated, e.g., rotated about a longitudinal axis thereof, with the pin 300' seated in a passageway thereof, to attempt to position the indicator mark 306' within range of one of more of the other windows' scales.

In the illustrated embodiment, as shown in FIG. 19, the indicator mark 306' is adjacent "32" on the first scale 116a', e.g., the scale indicating socket depth, thereby indicating that a 32 mm socket depth is an appropriate socket size to be formed in the femur 400 for a 15 mm size implant (as indicated by the size indicator 118') based on this patient's particular anatomy. The indicator mark 306' is also adjacent "22" on the second scale 116b', e.g., the scale indicating GIT, thereby indicating that an interface between a graft and the bone tunnel 402 would be 22 mm for a 15 mm size implant (as indicated by the size indicator 118') based on this patient's particular anatomy. The predetermined distance 306d' of the indicator mark 306' from the pin's tip can allow the first and second scales 116a', 116b' to accurately indicate the socket depth and the GIT since a distance between the indicator mark 306' and the pusher shaft 200' abutting the femur 400 is a known value, the predetermined distance 306d' minus the bore depth 206d'. However, as mentioned above, a gauge member can include one or more scales indicating characteristics other than socket depth and the GIT, such as a total bone tunnel length.

If the gauge member 100' included one or more additional windows formed therein, each of the one or more additional windows having at least one scale associated therewith, a position of the indicator mark 306' can be determined relative to each of the one or more additional windows and their respective scale(s). The indicator mark's position relative to each of the one or more additional windows and their respective scale(s) can provide additional information regarding the 15 mm size implant (if any of the one or more additional windows correspond to a 15 mm size implant and those one or more windows have scale(s) indicating information other than socket depth and GIT) or information regarding a differently sized implant. The indicator mark 306' may not be visible through multiple windows simultaneously, e.g., because one or more of the windows may face "down." The gauge member can be repositioned relative to the pin 300', e.g., rotated about the gauge member's longitudinal axis and the pin's longitudinal axis, so as to move each of the gauge member's windows to a different position relative to the indicator mark 306'. For example, the gauge member 100 of FIGS. 1 and 2 having two windows equidistantly spaced apart from one another can be rotated 180° to move a one of the windows 112a, 112b to the other of the windows' previous position.

The gauge member 100' can be removed from the patient's body, and a second gauge member (not shown) can be advanced into the patient's body and abut the femur 400 similar to that discussed above regarding the gauge member 100'. The second gauge member can include one or more windows formed therein that correspond to one or more implants having a different size than the window 112' of the gauge member 100' and/or can include one or more windows formed therein that correspond to a same-sized implant as the window 112' of the gauge member 100' but have one or more different scales such that the second gauge member can provide different information regarding the implant than the gauge member 100'. Thus, differently sized implants can be compared during performance of the surgical procedure without performance of any mathematical calculations and/or multiple characteristics associated with the bone tunnel 402 can be determined during performance of the surgical procedure without performance of any mathematical calculations.

Having determined the characteristic indicated by the first scale 116a' and/or the characteristic indicated by the second scale 116b', and having determined any other characteristic(s) (e.g., using one or more additional gauge members and/or using a single gauge member's multiple windows), an implant (not shown) can be implanted into the patient's body. The implant can have the 15 mm size indicated by the indicator mark 118', or the implant can have another size indicated by another gauge member's indicator size, should the 15 mm size be determined to be inadequate for any reason based on the characteristics determined by comparing the indicator mark's position with one or both of the scales 116a', 116b'.

A socket (not shown) can be formed in the femur 400 and be configured to seat a graft (not shown) therein, as will be appreciated by a person skilled in the art. The socket be formed so as to have a depth as determined using the indicator mark 306' and the first scale 116a'. The socket can be formed in any number of ways, as will also be appreciated by a person skilled in the art. The socket can be formed in a portion of the bone tunnel 402 adjacent the second end 406 of the bone tunnel 402 and can have a diameter greater than a remainder of the bone tunnel 402.

The implant can be implanted into the patient's body in a variety of ways, as will be appreciated by a person skilled in the art. As mentioned above, the implant can include an elongated body having a graft (not shown) attached thereto. The elongated body can be passed into the second end 406 of the bone tunnel 402 in a first position relative to the bone tunnel 402, advance through the bone tunnel 402, and exit the bone tunnel 402 through the first end 410 of the bone tunnel 402. The implant can pull the graft into the bone tunnel 402, e.g., into a socket formed adjacent the bone tunnel's second end 406 at a depth indicated by the first scale 116a'. The graft can be positioned within the bone tunnel 402, e.g., within the socket, having an interface with the bone tunnel 402 as indicated by the second scale 116b'. Positioned outside the femur 400, the implant can be moved from the first position to a second position relative to the bone tunnel 402. In the second position, the implant can abut the femur's surface adjacent the bone tunnel's first end 410, thereby securing the graft within the bone tunnel 402, e.g., within the socket.

In an exemplary embodiment, the gauge member 100', the pusher shaft 200', and the pin 300' can be removed from the patient's body prior to formation of the socket and prior to implantation of the implant. The gauge member 100', the pusher shaft 200', and the pin 300' can be removed from the patient's body in a variety of different orders, e.g., first the gauge member 100', second the pusher shaft 200', and third the pin 300'.

A person skilled in the art will appreciate that the present invention has application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims.

What is claimed is:
1. A surgical method, comprising:
 advancing a pin through a tunnel formed in a bone such that a first portion of the pin extends outwardly from a first end of the tunnel, and a second portion of the pin extends outwardly from a second end of the tunnel;
 positioning an elongate pusher shaft over the first portion of the pin and in abutment with a surface of the bone adjacent the first end of the tunnel;

advancing an elongate gauge member over the second portion of the pin and in abutment with a surface of the bone adjacent the second end of the tunnel; and positioning an indicator mark formed on the pin within a window formed in the gauge member, a position of the indictor mark relative to the window indicating a characteristic related to the tunnel when the pusher shaft abuts the surface of the bone adjacent the first end of the tunnel and the gauge member abuts the surface of the bone adjacent the second end of the tunnel.

2. The method of claim 1, wherein the characteristic is at least one of a total depth of the tunnel, a depth of a portion of the tunnel having a larger diameter than another portion of the tunnel, and an amount of interface between a graft and the tunnel.

3. The method of claim 1, further comprising selecting a size of a graft to position within the tunnel based on the position of the indictor mark relative to the window, and advancing the graft having the selected size into the tunnel.

4. The method of claim 1, further comprising adjusting the gauge member relative to the pin, a position of the indictor mark relative to a second window formed in the gauge member indicating another characteristic related to the tunnel when the pusher shaft abuts the surface of the bone adjacent the first end of the tunnel and the gauge member abuts the surface of the bone adjacent the second end of the tunnel.

5. The method of claim 1, wherein positioning the pusher shaft comprises pushing the pin and the pusher shaft toward the second end of the tunnel.

6. The method of claim 1, wherein advancing the gauge member comprises passing the pin through a cannulated interior of the gauge member.

* * * * *